US008933071B2

(12) United States Patent
Crispino et al.

(10) Patent No.: US 8,933,071 B2
(45) Date of Patent: Jan. 13, 2015

(54) DIMETHYL FASUDIL FOR INDUCING POLYPLOIDIZATION OF MEGAKARYOCYTES AND FOR TREATING BLOOD AND BONE MARROW DISEASES AND DISORDERS

(75) Inventors: John D. Crispino, Wilmette, IL (US); Qiang Wen, Chicago, IL (US); Zan Huang, Chicago, IL (US); Andrew M. Stern, Boston, MA (US); Robert J. Gould, Beverly, MA (US)

(73) Assignees: Northwestern University, Evanston, IL (US); Massachusetts Institute of Technology, Cambridge, MA (US)

( * ) Notice: Subject to any disclaimer, the term of this patent is extended or adjusted under 35 U.S.C. 154(b) by 1033 days.

(21) Appl. No.: 12/613,996

(22) Filed: Nov. 6, 2009

(65) Prior Publication Data

US 2010/0120750 A1      May 13, 2010

Related U.S. Application Data

(60) Provisional application No. 61/112,445, filed on Nov. 7, 2008.

(51) Int. Cl.
*A61K 31/551*   (2006.01)
*A61K 31/5513*  (2006.01)

(52) U.S. Cl.
CPC ........... *A61K 31/5513* (2013.01); *A61K 31/551* (2013.01)
USPC ........................................................ 514/218

(58) Field of Classification Search
None
See application file for complete search history.

(56) References Cited

U.S. PATENT DOCUMENTS

| 6,153,608 A * | 11/2000 | Hidaka et al. ................ 514/218 |
| 2007/0185069 A1* | 8/2007 | Plum et al. ..................... 514/182 |
| 2008/0255244 A1* | 10/2008 | Collins et al. ................. 514/725 |

FOREIGN PATENT DOCUMENTS

WO      2006001954      1/2006

OTHER PUBLICATIONS

"The rho-kinase inhibitors Y-27632 and fasudil act synergistically with imatinib to inhibit the expansion of ex vivo CD34+ CML progenitor cells" by Burthem et al., Leukemia 21, 1708-14 (Jun. 2007).*
Fasudil CAS Registry Record (retrieved Mar. 2013).*
"Rho GTPase expression in tumourigenesis: evidence for a significant link" by Pulgar et al., BioEssays 27, 602-13 (2005).*
"Proerectile Effects of the Rho-Kinase Inhibitor (S)-(+)-2-Methyl-1-[(4-methyl-5-isoquinolinyl)sulfonyl]homopiperazine (H-1152) in the Rat Penis" by Teixeira et al., J. Pharmacol. Exp. Ther. 315, 155-62 (2005).*
"Acute Megakaryoblastic Leukemia" by Grassmann et al., Leukemia & Lymphoma 18, 69-73 (1995).*
Al-Ahmari et al., "Long-term results of an ultra low-dose cytarabine-based regiment for the treatment of acute megakaryoblastic leukaemia in children with Down syndrome", British Journal of Haematology, 2006, 133:646-648.
Barnard et al., "Comparison of Childhood Myelodysplastic Syndrome, AML FAB M6 or M7, CCG 2891: Report From the Children's Oncology Group", Pediatric Blood and Cancer Journal, 2007, 49:17-22.
Bourquin et al., "Identification of distinct molecular phenotypes in acute megakaryoblastic leukemia by gene expression profiling", PNAS, Feb. 28, 2006, 103(9):3339-3344.
Chen et al., "The May-Hegglin anomaly gene MYH9 is a negative regulator of platelet biogenesis modulated by the Rho-ROCK pathway", Blood, Jul. 1, 2007, 110(1):171-179.
Dombret et al., "InVivo Thrombin and Plasmin Activities in Patients with Acute Promyelocytic Leukemia (APL): Effect of All-Trans Retinoic Acid (ATRA) Therapy", Leukemia, 1995, 9:19-24.
Fridman et al., "Discovery and Preclinical Characterization of INCB018424, a Selective JAK2 Inhibitor for the Treatment of Myeloproliferative Disorders", Blood, 2007, 110:Abstract 3538.
Gurbuxani et al., "Recent insights into the mechanisms of myeloid leukemogenesis in Down syndrome", Blood, Jan. 15, 2004, 103(2):399-406.
Hahn et al., "Syk Is a New Target for AML Differentiation", Blood, 2007, 110:Abstract 209.
Horak et al., "GATA-1 binding sites mapped in the beta-globin locus by using mammalian chip-chip analysis", PNAS, Mar. 5, 2002, 99(5):2924-2929.
Meng-Er et al., "Use of All-Trans Retinoic Acid in the Treatment of Acute Promyelocytic Leukemia", Blood, Aug. 1988, 72(2):567-572.
Huang et al., "STAT1 promotes megakaryopoiesis downstream of GATA-1 in mice", Journal of Clinical Investigation, Dec. 2007, 117(12):3890-3899.
Jelinek et al., "JAK2 mutation 1849G>T is rare in acute leukemias but can be found in CMML, Philadelphia chromosome-negative CML, and megakaryocytic leukemia", Blood, Nov. 15, 2005, 106(10):3370-3373.
Jing et al., "The Design of Selective and Non-selective Combination Therapy for Acut Promyelocytic Leukemia", CTMI, 2007, 313:245-269.
Klussman et al., "Janus kinase mutations in the development of acute megakaryoblastic leukemia in children with and without Down's syndrome", Leukemia, 2007,21:1584-1587.
Lannutti et al., "Induction of polyploidization in leukemic cell lines and primary bone marrow by Src kinase inhibitor SU6656", Blood, May 15, 2005, 105(10):3875-3878.

(Continued)

*Primary Examiner* — Theodore R West
(74) *Attorney, Agent, or Firm* — Andrus Intellectual Property Law, LLP

(57) ABSTRACT

Disclosed are methods for inducing polyploidization of megakaryocyte cells and for promoting differentiation of megakaryocyte cells into platelet-producing cells. The methods may be utilized for treating blood and bone marrow diseases and disorders in a subject in need thereof and for identifying agents for treating blood and bone marrow diseases and disorders.

12 Claims, 11 Drawing Sheets

(56) References Cited

OTHER PUBLICATIONS

Levine et al., "JAK-2 mutations and their relevance to myeloproliferative disease", Current Opinion in Hematology, 2007, 14:43-47.

Li et al., "Developmental stage-selective effect of somatically mutated leukemogenic transcription factor GATA1", Nature Genetics, Jun. 2005, 37(6):613-619.

Mizutani et al., "Successful second cord blood transplantation using fludarabine and cyclophophamide as a preparative regimen for graft rejection following reduced-intensity cord blood transplantation", Bone Marrow Transplantation, 2007, 40:85-87.

Muntean et al., "Differential requirements for the activation domain and FOG-interaction surface of GATA-1 in megakayocyte gene expression and development", Blood, Aug. 15, 2005, 106(4):1223-1231.

Muntean et al., "Cyclin D-Cdk4 is regulated by GATA-1 and required for megakaryocyte growth and polyploidization", Blood, Jun. 15, 2007, 109(12):5199-5207.

Mercher et al., "The OTT-MAL fusion oncogene activates RBPJ-mediated transcription and induces acute megakaryoblastic leukemia in a knockin mouse model", Journal of Clinical Investigation, Apr. 2009, 119(4):852-864.

Pagano et al., "Acute megakaryoblastic leukemia: expreience of GIMEMA trials", Leukemia, 2002, 16:1622-1626.

Ravid et al., "Roads to Polyploidy: The Megakaryocyte Example", Journal of Cellular Physiology, 2002, 190:7-20.

Rylski et al., "GATA-1-Mediated Prolifereation Arrest during Erythroid Maturation", Molecular and Cellular Biology, Jul. 2003, 23(14):5031-5042.

Shivdasani et al., "A lineage-selective knockout establishes the critical role of transcription factor GATA-1 in megakaryocyte growth and platelet development", EMBO Journal, 1997, 16(13):3965-3973.

Steensma et al., "JAK2 V617F is a rare finding in de novo acute myeloid leukemia, but STAT3 activation is common and remains unexplained", Leukemia, 2006, 20:971-978.

Tallman et al., "Acute megakaryocytic leukemia: the Eastern Cooperative Oncology Group experience", Blood, Oct. 1, 2000, 96(7):2405-2411.

Verstovsek et al., "INCB081424, an Oral, Selective JAK2 Inhibitor, Shows Significant Clinical Activity in a Phase I/II Study in Patients with Primary Myelofibrosis (PMF) and Post Polycythemia Vera/Essential Thrombocythemia Myelofibrosis (Post-PV/ET MF)", Blood, 2007, 110:Abstract 558.

Vyas et al., "Consequences of GATA-1 Deficiency in Megakaryocytes and Platelets", Blood, May 1, 1999, 93(9):2867-2875.

Walters et al., "Activating alleles of JAK3 in acute megakaryoblastic leukemia", Cancer Cell, Jul. 2006, 10:65-75.

Warrell et al., "Differentiation Therapy of Acute Promyelocytic Leukemia with Tretinoin (All-Trans-Retinoic Acid)", New England Journal of Medicine, 1991, 324(20):1385-1393.

Wechsler et al., "Acquired mutations in GATA1 in the megakaryoblastic leukemia of Down syndrom", Nature Genetics, Sep. 2002, 32:148-152.

Welch et al., "Global regulation of erythroid gene expression by transcription factor GATA-1", Blood, Nov. 15, 2004, 104(10)3136-3147.

Wickrema et al., "Erythroid and megakaryocytic transformation", Oncogene, 2007, 26:6803-6815.

Zipursky, "Transient Leukaemia—A Benign Form of Leukaemia in Newborn Infants with Trisomy 21", British Journal of Haematology, 2003, 120:930-938.

Liao et al., "Rho Kinase (ROCK) Inhibitors", J Cardiovasc Pharmacol., Jul. 2007, 50(1):17-24.

\* cited by examiner

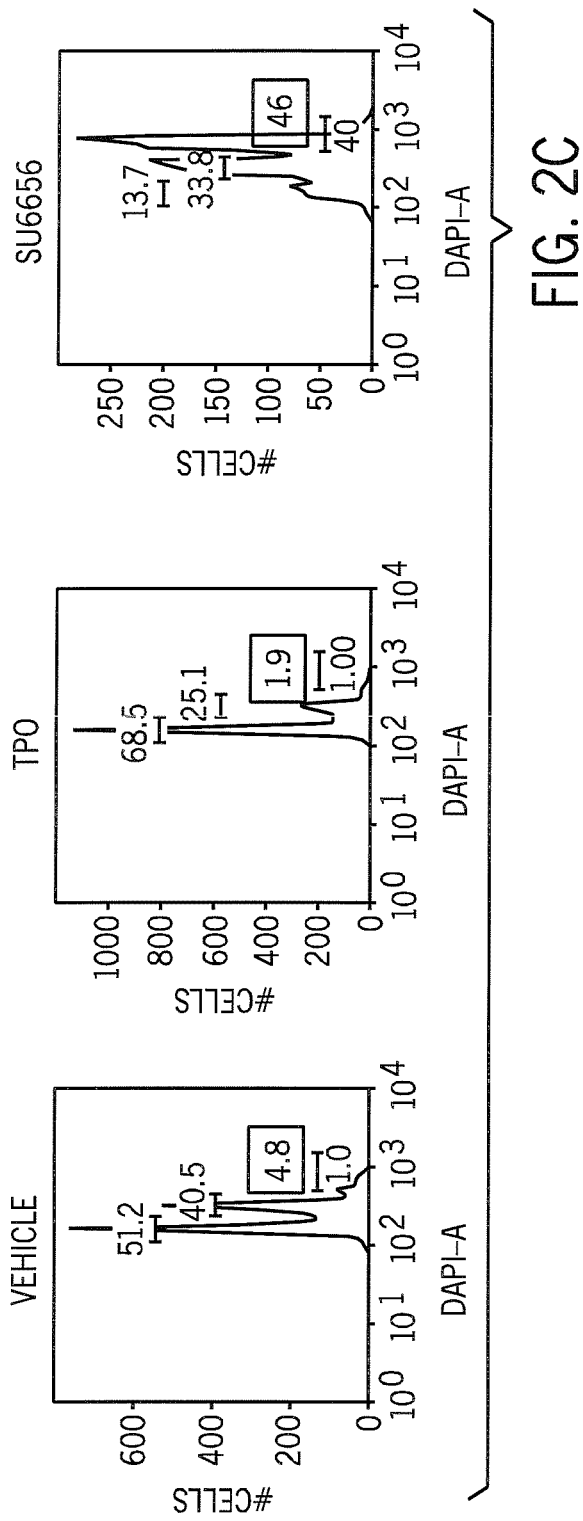
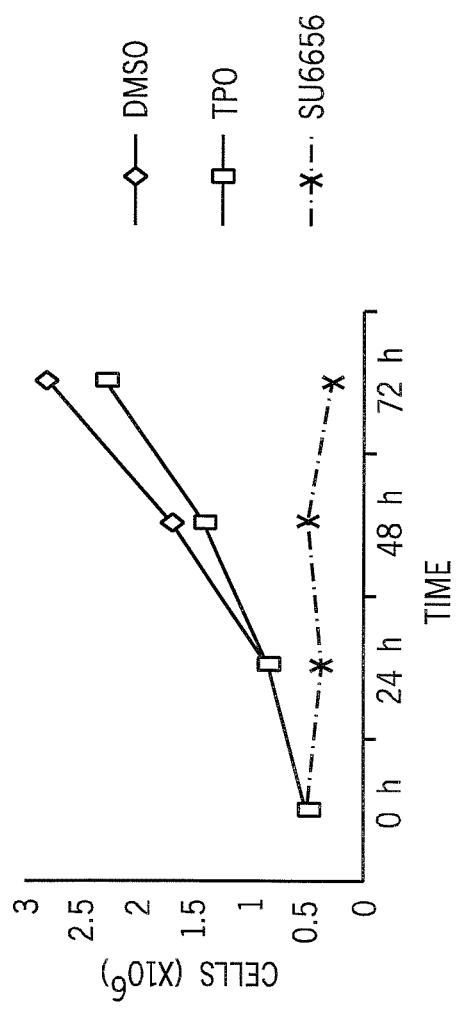
FIG. 2C
FIG. 2D

DIMETHYL FASUDIL FOR INDUCING POLYPLOIDIZATION OF MEGAKARYOCYTES AND FOR TREATING BLOOD AND BONE MARROW DISEASES AND DISORDERS

CROSS-REFERENCE TO RELATED APPLICATIONS

The present application claims the benefit under 35 U.S.C. §119(e) to U.S. Provisional Application No. 61/112,445, filed on Nov. 7, 2008, the content of which is incorporated herein by reference in its entirety.

BACKGROUND

The field of the invention relates to methods for inducing polyploidization of megakaryocytes and for treating blood and bone marrow diseases and disorders including leukemias. The field of the invention also relates to methods for identifying agents for treating blood and bone marrow diseases and disorders including leukemias.

Leukemia is a disease that develops when blood cell precursors grow excessively. There are many different forms of leukemia, which are classified by the type of blood cell that is affected or by the genetic abnormality that causes the disease. Unfortunately, there is no one treatment that works for all types, and in general, the most effective therapies are specifically targeted to the molecular causes of each disease. One very aggressive form of blood cancer for which there are few promising treatment options is Acute Megakaryocytic Leukemia (AMKL). This malignancy, which is generally fatal within one year of diagnosis, is caused by the uncontrolled growth of megakaryocytes, the cells that release platelets into the bloodstream to control bleeding. New treatments for leukemias such as AMKL are desirable.

SUMMARY

Disclosed are methods for inducing polyploidization of megakaryocyte cells and for promoting differentiation of megakaryocyte cells into platelet-producing cells. The methods may be utilized for treating blood and bone marrow diseases and disorders and for identifying agents for treating blood and bone marrow diseases and disorders.

The disclosed methods may include contacting megakaryocyte cells and an effective amount of a compound which induces, promotes, or causes polyploidization. In some embodiments, the methods may include contacting megakaryocyte cells and an effective amount of a compound having a Formula I:

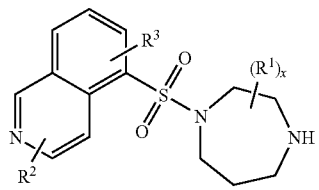

where:

$R^1$ are each independently selected from hydrogen; halogen (e.g., fluoro, chloro, bromo, or iodo); $C_{1-6}$ branched or straight-chain alkyl; $C_{2-6}$ alkenyl; $C_{2-6}$ alkynyl, and benzyl;

x is 0, 1, 2, 3, 4, or 5;

$R^2$ is hydrogen; halogen (e.g., fluoro, chloro, bromo, or iodo); $C_{1-6}$ branched or straight-chain alkyl; $C_{2-6}$ alkenyl; or $C_{2-6}$ alkynyl; and $R^3$ is hydrogen; halogen (e.g., fluoro, chloro, bromo, or iodo); $C_{1-6}$ branched or straight-chain alkyl; $C_{2-6}$ alkenyl; or $C_{2-6}$ alkynyl. For example, an "effective amount" may be an amount of the compound which induces, promotes, or causes polyploidization. Preferably, the compound has a Formula II, III, IV, or V:

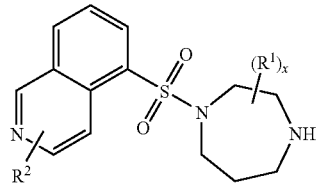

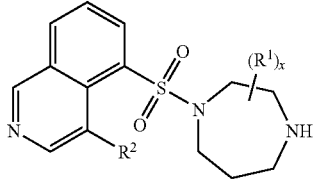

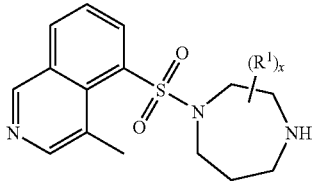

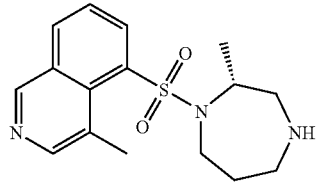

In even further embodiment, the compound having Formula I, II, III, IV, or V may be a Rho kinase inhibitor (i.e., a compound exhibiting Rho kinase inhibitor activity).

In other embodiments, the compound may be JAK3 Inhibitor VI having a Formula VI:

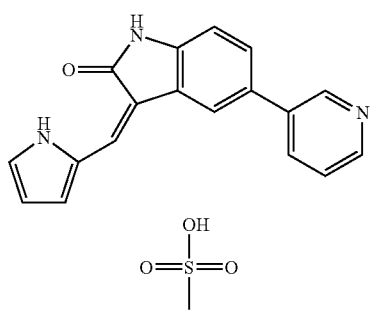

For example, in the presently contemplated methods an effective amount of the JAK3 Inhibitor VI for inducing, promoting, or causing polyploidization may be contacted with megakaryocyte cells.

The disclosed methods may specifically induce polyploidization of megakaryocyte cells. In some embodiments, the disclosed methods may induce polyploidization of megakaryocyte cells without significantly affecting the growth of non-megakaryocyte cells (e.g., without significantly affecting the growth of CD41$^-$ cells).

The disclosed methods may promote differentiation of megakaryocyte cells. In some embodiments, the disclosed methods may promote differentiation of megakaryocyte cells into platelet-producing cells.

The disclosed methods may include methods for reducing abnormal or malignant megakaryocyte cells in blood or bone marrow. In some embodiments, contemplated methods include methods whereby blood or bone marrow is contacted with an effective amount of a compound having any of Formulae I-VI.

Further disclosed are methods for treating a blood or bone marrow disease or disorder in a patient in need thereof. The methods may include administering an effective amount of a pharmaceutical composition for inducing polyploidization of megakaryocytes to the patient in which the pharmaceutical composition comprises as an active ingredient a compound having any of Formulae I-VI, or an analog or derivative thereof. In some embodiments, suitable compounds for use in the methods for treating a blood or bone marrow disease or disorder may include compounds having any of Formulae I-VI as disclosed herein. In some embodiments, the methods may result in increasing platelet counts in the patient.

DETAILED DESCRIPTION

Figure 1:
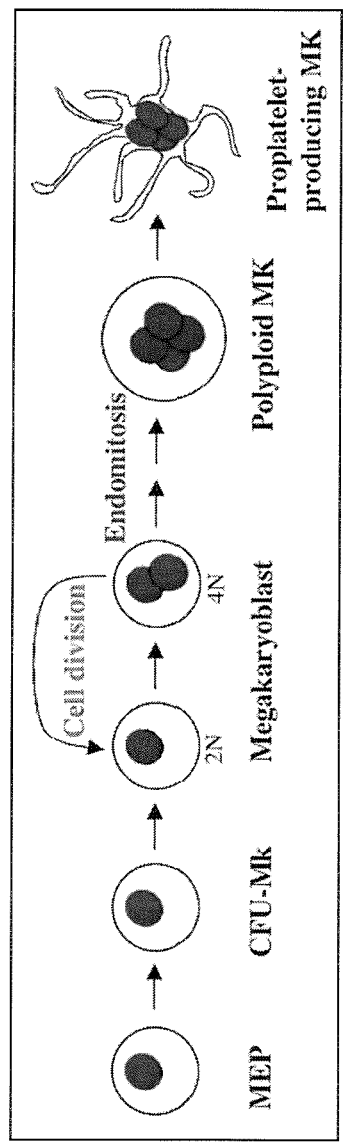
FIG. 1 illustrates that megakaryocyte maturation proceeds in an ordered fashion from the Megakaryocyte-Erythroid Precursor (MEP) through platelet-producing cells.
Figure 2A:
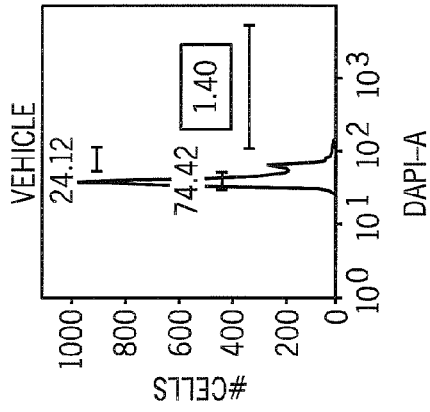
FIG. 2 illustrates that SU6656 induces polyploidization and proliferative arrest of megakaryocytic leukemia cells. (A) Y10, (B) GIME, and (C) CMK cells were grown in the presence of TPO, SU6656, or vehicle (DMSO) for 72 hours. DNA content was measured by flow cytometry. The percentages of cells that reach a DNA content of ≥8N are boxed in A and C, those equal to 8N are boxed in B. D) CMK cells were grown as in (C), and cell numbers were enumerated at 0, 24, 48 and 72 h.
Figure 2A:
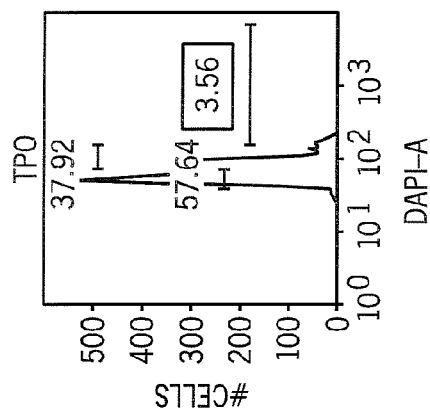
Figure 2A:
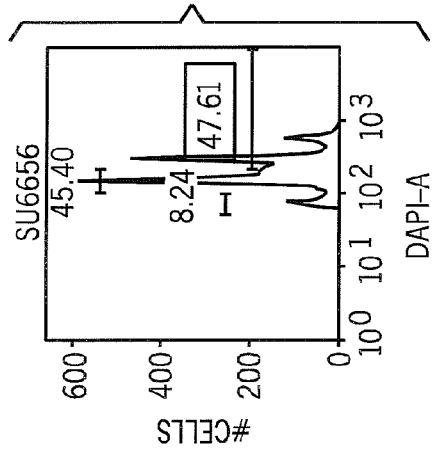
Figure 2B:
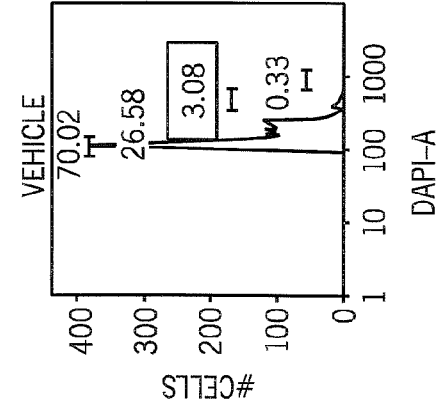
Figure 2B:
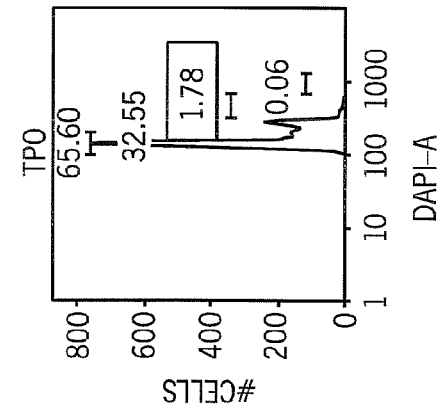
Figure 2B:
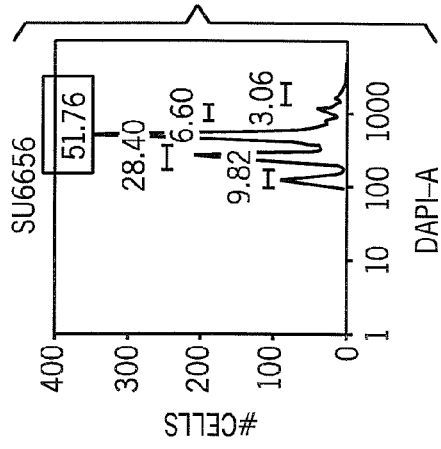

The disclosed subject matter further may be described utilizing terms as defined below.

Unless otherwise specified or indicated by context, the terms "a", "an", and "the" mean "one or more."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising."

The terms "patient" and "subject" may be used interchangeably herein. A patient may be a human patient. A patient may refer to a human patient having or at risk for acquiring a blood or bone marrow disease or disorder, which may include a proliferative blood or bone marrow disease or disorder such as leukemia. Representative diseases and disorders include but are not limited to Acute Megakaryoblastic Leukemias, Myeloproliferative Diseases, Myelodysplastic Syndromes, and Acute Myeloid Leukemias. Acute Megakaryoblastic Leukemias may include but are not limited to AMKL associated with mutagenesis of GATA1 in Down syndrome, pediatric AMKL associated with a (1:22) translocation, and adult AMKL associated with mutations in JAK2 or JAK3. Myeloproliferative Diseases may include but are not limited to primary myelofibrosis (PMF), essential thrombocythemia (ET), and polycythemia vera (PV).

As used herein, "polyploidization" refers to the process whereby cells acquire more than two homologous sets of chromosomes. Polyploidization may occur by endomitosis in which mitosis takes place without dissolution of the nuclear membrane and without cytoplasmic division, resulting in repeated doubling of the number of chromosomes within the nucleus of the cell. The contemplated methods for inducing, promoting, or causing polyploidization of megakaryocyte cells may be performed in vivo or in vitro.

As used herein, "megakaryocyte cells" refer to hematopoietic cells that are responsible for the production of platelets or platelet-like fragments which are necessary for blood clotting. Megakaryocyte cells may include megakaryocyte progenitors which are capable of being induced to differentiate into platelet-producing cells. The contemplated methods for inducing, promoting, or causing differentiation of megakaryocyte cells into platelet-producing cells may be performed in vivo or in vitro. Megakaryocyte cells may include abnormal, malignant, immortalized, immature, or dysplastic megakaryocyte cells. "Dysplastic" refers to cells that are not malignant but exhibit defective growth and/or differentiation characteristics with respect to normal cells. Megakaryocyte cells may be isolated from a biological sample such as blood, umbilical cord blood, and bone marrow. Megakaryocyte cells may include murine and human megakaryoblastic cell lines such as L8057, GIME, Meg-01, CHRf-288, CMK, CMS, CMY, and MKLP1.

In some embodiments, suitable compounds for the methods contemplated herein include compounds having any of Formulae I-VI, or analogs or derivatives thereof. Suitable compounds for the methods contemplated herein may include stereoisomers, enantiomers, or epimers of compounds having any of Formulae I-VI. Suitable compounds for the methods may include salts, esters, amides, or solvates thereof of compounds having any of Formulae I-VI. Preferably, a suitable compound utilized in the disclosed methods has a relatively low EC50 with respect to inducing polyploidization of megakaryocytes as disclosed herein (e.g., an EC50 less that is than about 10 μm, preferably an EC50 that is less than about 5 or even more preferably an EC50 that is less than about 1 μM).

In some embodiments, a suitable compound for the methods contemplated herein may include Rho kinase inhibitor (i.e., "ROCK Inhibitor") or analogs or derivatives thereof (e.g., analogs or derivatives thereof having Rho kinase inhibitory activity). As utilized herein, "ROCK Inhibitor" may alternately be referred to as dimethylfasudil ("DMF"). Referring to the PubChem Database provided by the National Center for Biotechnology Information (NCBI) of the National Institute of Health (NIH), Rho kinase inhibitor is referenced by compound identification (CID) number 16760633. Analogs or derivatives of Rho kinase inhibitor may include salts, esters, amides, or solvates thereof. Furthermore, analogs or derivatives of Rho kinase inhibitor may include "similar compounds" as defined at the PubChem Database, which include but are not limited to compounds referenced by CID Nos.: 16760633, 1150225, 21948562, 21948557, 22121964, 22121951, 22121949, 22121916, 22121910, 22121894, 21948574, 9885022, 9841610, 9841609, 22121970, 22121965, 22121961, 22121952, 22121950, 22121917, 22121911, 22121897, 22121895, 21948558, 17808898, 17808878, 15487114, 9951686, 9885023, 9841611, 448043, 22121962, 22121947, 22121918, 24752910, 22393224, 22393203, 22393173, 22121971, and 22121968, which entries are incorporated herein by reference in their entireties. Preferably, analogs and derivatives of Rho kinase inhibitor induce, promote, or cause polyploidization of megakaryocyte cells or induce, promote, or cause megakaryocytes cells to differentiate into platelet-producing cells.

In some embodiments, a suitable compound for the methods contemplated herein may include JAK3 Inhibitor VI or analogs or derivatives thereof (e.g., analogs or derivatives thereof exhibiting JAK3 inhibitory activity). Referring to the PubChem Database provided by the National Center for Biotechnology Information (NCBI) of the National Institute of Health (NIH), JAK3 Inhibitor VI is referenced by compound identification (CID) number 16760524. Analogs or derivative of JAK3 Inhibitor VI may include salts, esters, amides, or solvates thereof. Furthermore, analogs or derivatives of JAK3 Inhibitor VI may include "similar compounds" as defined at the PubChem Database, which include but are not limited to compounds referenced by CID Nos.: 1676052, 9947841, 11449069, 11200499, 18363918, 12822470, 12822483, 11661489, 20222392, 20222398, 9857885, 9879744, 24906278, 24906279, 18359288, and 18359279, which entries are incorporated herein by reference in their entireties. Preferably, analogs and derivatives of JAK3 Inhibitor VI Induce, promote, or cause polyploidization of megakaryocyte cells or induce, promote, or cause megakaryocytes cells to differentiate into platelet-producing cells.

Other compounds for inducing polyploidization and differentiation of megakaryocyte progenitor cells are known in the art. For example, the compound SU6656 is thought to induce polyploidization and differentiation of megakaryocyte progenitor cells. (See, e.g., published international PCT application No. WO 2006/001954, which is incorporated by reference herein in its entirety.)

It will be appreciated that the compounds disclosed herein (e.g., compounds having any of Formulae I-VI) may have several chiral centers, and stereoisomers, epimers, and enantiomers are contemplated. The compounds may be optically pure with respect to one or more chiral centers (e.g., some or all of the chiral centers may be completely in the S configuration; some or all of the chiral centers may be completely in the R configuration; etc.). Additionally or alternatively, one or more of the chiral centers may be present as a mixture of configurations (e.g., a racemic or another mixture of the R configuration and the S configuration). Compositions comprising substantially purified stereoisomers, epimers, or enantiomers of compound having any of Formulae I-VI are contemplated herein (e.g., a composition comprising at least about 90%, 95%, or 99% pure stereoisomer, epimer, or enantiomer.)

As indicated above, pharmaceutically acceptable salts of the compounds are contemplated and also may be utilized in the disclosed methods. For example, a carboxylic acid group of the disclosed compounds may be deprotonated and an amino group of the disclosed compounds may be protonated. The term "pharmaceutically acceptable salt" as used herein, refers to salts of the compounds which are substantially non-toxic to living organisms. Typical pharmaceutically acceptable salts include those salts prepared by reaction of the compounds as disclosed herein with a pharmaceutically acceptable mineral or organic acid or an organic or inorganic base. Such salts are known as acid addition and base addition salts. It will be appreciated by the skilled reader that most or all of the compounds as disclosed herein are capable of forming salts and that the salt forms of pharmaceuticals are commonly used, often because they are more readily crystallized and purified than are the free acids or bases.

Acids commonly employed to form acid addition salts may include inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of suitable pharmaceutically acceptable salts may include the sulfate, pyrosulfate, bisulfate, sulfite, bisulfate, phosphate, monohydrogenphosphate, dihydrogenphosphate, metaphosphate, pyrophosphate, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleat-, butyne-.1,4-dioate, hexyne-1,6-dioate, benzoate, chlorobenzoate, methylbenzoate, hydroxybenzoate, methoxybenzoate, phthalate, xylenesulfonate, phenylacetate, phenylpropionate, phenylbutyrate, citrate, lactate, alpha-hydroxybutyrate, glycolate, tartrate, methanesulfonate, propanesulfonate, naphthalene-1-sulfonate, naphthalene-2-sulfonate, mandelate, and the like.

Base addition salts include those derived from inorganic bases, such as ammonium or alkali or alkaline earth metal hydroxides, carbonates, bicarbonates, and the like. Bases useful in preparing such salts include sodium hydroxide, potassium hydroxide, ammonium hydroxide, potassium carbonate, sodium carbonate, sodium bicarbonate, potassium bicarbonate, calcium hydroxide, calcium carbonate, and the like.

It should be recognized that the particular counter-ion forming a part of any salt of a compound disclosed herein is usually not of a critical nature, so long as the salt as a whole is pharmacologically acceptable and as long as the counterion does not contribute undesired qualities to the salt as a whole. Undesired qualities may include undesirably solubility or toxicity.

It will be further appreciated that the disclosed compounds can be in equilibrium with various inner salts. For example, inner salts includes salts wherein the compound includes a deprotonated carboxyl group and a protonated amino group.

Pharmaceutically acceptable esters and amides of the compounds can also be employed in the compositions and methods disclosed herein. Examples of suitable esters include alkyl, aryl, and aralkyl esters, such as methyl esters, ethyl esters, propyl esters, dodecyl esters, benzyl esters, and the like. Examples of suitable amides include unsubstituted amides, monosubstituted amides, and disubstituted amides, such as methyl amide, dimethyl amide, methyl ethyl amide, and the like.

In addition, the methods disclosed herein may be practiced using solvate forms of the compounds or salts, esters, and/or amides, thereof. Solvate forms may include ethanol solvates, hydrates, and the like.

The methods disclosed herein may be practiced in vitro or in vivo. More particularly, the methods disclosed herein may be used in vivo to treat a blood or bone marrow disease or disorder. In the case where the methods disclosed herein are carried out in vivo, for example, where the megakaryocytes are present in a human subject, contacting can be carried out by administering a therapeutically effective amount of the compound to the human subject, for example, by directly injecting the compound into the subject in the vicinity of the megakaryocytes to be contacted or by other suitable means of administration. Details with regard to this and other methods for administering compounds in accordance with the methods disclosed herein are further described below.

The disclosed compounds may be contacted with megakaryocyte cells in methods for inducing polyploidization of megakaryocyte cells and in methods for promoting differentiation of megakayrocyte cells. In some embodiments, the amount of the disclosed compounds that is effective to induce polyploidization of megakayrocyte cells or to promote differentiation of megakayrocyte cells is about 0.05-50 µM (or about 0.05-10 µM, or about 0.05-1 µM).

Also disclosed are methods of treating a blood or bone marrow disease or disorder in a subject. The methods may include administering to the subject an effective amount of a compound that induces polyploidization of megakaryocytes.

The disclosed compounds may be used to prepare pharmaceutical compositions for administering in methods of treating a "blood or bone marrow disease or disorder." As used herein, "blood or bone marrow disease or disorder" is meant to include proliferative blood or bone marrow diseases or disorders. Examples of such blood or bone marrow diseases or disorders include, but are not limited to, leukemias (e.g., Acute Megakaryoblastic Leukemia (AMKL) and Acute Myeloid Leukemia (AML)), Myeloproliferative Diseases (e.g., primary myelofibrosis (PMF), essential thrombocythemia (ET), and polycythemia vera (PV)), Myelodysplastic Syndromes, thrombocytopenias, and essential thrombocytoses.

Suitable patients and subjects for the disclosed methods include, for example mammals, such as humans, monkeys, dogs, cats, horses, rats, and mice. Suitable human subjects include, for example, those who have previously been determined to be at risk of having or developing a blood or bone marrow disease or disorder as contemplated herein. Still other suitable human subjects include, for example, those who have not been diagnosed as having and/or who have not previously been determined to be at risk of having or developing a blood or bone marrow disease or disorder.

As used herein, the terms "treating" or "to treat" each mean to alleviate symptoms, eliminate the causation of resultant symptoms either on a temporary or permanent basis, and/or to prevent or slow the appearance or to reverse the progression or severity of resultant symptoms of the named disorder. As such, the methods disclosed herein encompass both therapeutic and prophylactic administration.

As used herein the term "effective amount" refers to the amount or dose of the compound, upon single or multiple dose administration to the subject, which provides the desired effect in the subject under diagnosis or treatment. The disclosed methods may include administering an effective amount of the disclosed compounds (e.g., as present in a pharmaceutical composition) for treating a blood or bone marrow disease or disorder in the subject, whereby the effective amount induces, promotes, or causes polyploidization of megakaryocytes in the subject or induces, promotes, or causes megakaryocytes cells to differentiate into platelet-producing cells in the subject.

An effective amount can be readily determined by the attending diagnostician, as one skilled in the art, by the use of known techniques and by observing results obtained under analogous circumstances. In determining the effective amount or dose of compound administered, a number of factors can be considered by the attending diagnostician, such as: the species of the subject; its size, age, and general health; the degree of involvement or the severity of the blood or bone marrow disease or disorder involved; the response of the individual subject; the particular compound administered; the mode of administration; the bioavailability characteristics of the preparation administered; the dose regimen selected; the use of concomitant medication; and other relevant circumstances.

In some embodiments, a daily dose may contain from about 0.01 mg/kg to about 100 mg/kg (such as from about 0.05 mg/kg to about 50 mg/kg and/or from about 0.1 mg/kg to about 25 mg/kg) of each compound used in the present method of treatment. The dose may be administered under any suitable regimen (e.g., weekly, daily, twice daily).

The pharmaceutical compositions for use according to the methods as disclosed herein may include be a single compound as an active ingredient or a combination of compounds as active ingredients. For example, the methods disclosed herein may be practiced using a composition containing a single compound that induces polyploidization of megakaryocytes, or it can be practiced using a composition containing two or more compounds that induce polyploidization of megakaryocytes. The aforementioned compositions optionally may contain one or more other active ingredients that do not induce polyploidization of megakaryocytes. For example, the aforementioned compositions optionally may contain as active ingredients for treating a blood or bone marrow disease or disorder one or more compounds that do not induce polyploidization of megakaryocytes but otherwise treat the blood or bone marrow disease.

The disclosed compounds may be administered with other compounds known in the art for treating leukemias, myeloproliferative diseases, or myelodysplastic syndromes. In some embodiments, the disclosed compounds that induce polyploidization of megakaryocytes may be administered with a another active agent such as a JAK kinase inhibitor (e.g., CP-690550), a histone deacetylase (HDAC) inhibitor (e.g., FK228 or ITF2357), an hsp90 inhibitor (e.g., geldanamycin), or a drug from the immunomodulatory (IMiD) class of drugs (e.g., CC-5013 and CC-4047) to a patient having or at risk for developing leukemia (e.g., AMKL or AML), a myeloproliferative disease (MPD), or a myelodysplastic syndrome (MDS).

Oral administration is an illustrative route of administering the compounds employed in the compositions and methods disclosed herein. Other illustrative routes of administration include transdermal, percutaneous, intravenous, intramuscular, intranasal, buccal, intrathecal, intracerebral, or intrarectal routes. The route of administration may be varied in any way, limited by the physical properties of the compounds being employed and the convenience of the subject and the caregiver.

The compounds employed in the compositions and methods disclosed herein may be administered as pharmaceutical compositions and, therefore, pharmaceutical compositions incorporating the compounds are considered to be embodiments of the compositions disclosed herein. Such compositions may take any physical form which is pharmaceutically acceptable; illustratively, they can be orally administered pharmaceutical compositions. Such pharmaceutical compositions contain an effective amount of a disclosed compound, which effective amount is related to the daily dose of the compound to be administered. Each dosage unit may contain the daily dose of a given compound or each dosage unit may contain a fraction of the daily dose, such as one-half or one-third of the dose. The amount of each compound to be contained in each dosage unit can depend, in part, on the identity of the particular compound chosen for the therapy and other factors, such as the indication for which it is given. The pharmaceutical compositions disclosed herein may be formulated so as to provide quick, sustained, or delayed release of the active ingredient after administration to the patient by employing well known procedures.

Compositions can be formulated in a unit dosage form, each dosage containing from about 1 to about 500 mg of each compound individually or in a single unit dosage form, such as from about 5 to about 300 mg, from about 10 to about 100 mg, and/or about 25 mg. The term "unit dosage form" refers to a physically discrete unit suitable as unitary dosages for a patient, each unit containing a predetermined quantity of active material calculated to produce the desired therapeutic effect, in association with a suitable pharmaceutical carrier, diluent, or excipient.

The inert ingredients and manner of formulation of the pharmaceutical compositions are conventional. The usual methods of formulation used in pharmaceutical science may be used here. All of the usual types of compositions may be used, including tablets, chewable tablets, capsules, solutions, parenteral solutions, intranasal sprays or powders, troches, suppositories, transdermal patches, and suspensions. In general, compositions contain from about 0.5% to about 50% of the compound in total, depending on the desired doses and the type of composition to be used. The amount of the compound, however, is best defined as the "effective amount", that is, the amount of the compound which provides the desired dose to the patient in need of such treatment. The activity of the compounds employed in the compositions and methods disclosed herein are not believed to depend greatly on the nature of the composition, and, therefore, the compositions can be chosen and formulated primarily or solely for convenience and economy.

Capsules are prepared by mixing the compound with a suitable diluent and filling the proper amount of the mixture in capsules. The usual diluents include inert powdered substances (such as starches), powdered cellulose (especially crystalline and microcrystalline cellulose), sugars (such as fructose, mannitol and sucrose), grain flours, and similar edible powders.

Tablets are prepared by direct compression, by wet granulation, or by dry granulation. Their formulations usually incorporate diluents, binders, lubricants, and disintegrators (in addition to the compounds). Typical diluents include, for example, various types of starch, lactose, mannitol, kaolin, calcium phosphate or sulfate, inorganic salts (such as sodium chloride), and powdered sugar. Powdered cellulose derivatives can also be used. Typical tablet binders include substances such as starch, gelatin, and sugars (e.g., lactose, fructose, glucose, and the like). Natural and synthetic gums can also be used, including acacia, alginates, methylcellulose, polyvinylpyrrolidine, and the like. Polyethylene glycol, ethylcellulose, and waxes can also serve as binders.

Tablets can be coated with sugar, e.g., as a flavor enhancer and sealant. The compounds also may be formulated as chewable tablets, by using large amounts of pleasant-tasting substances, such as mannitol, in the formulation. Instantly dissolving tablet-like formulations can also be employed, for example, to assure that the patient consumes the dosage form and to avoid the difficulty that some patients experience in swallowing solid objects.

A lubricant can be used in the tablet formulation to prevent the tablet and punches from sticking in the die during manufacturing. The lubricant can be chosen from such slippery solids as talc, magnesium and calcium stearate, stearic acid, and hydrogenated vegetable oils.

Tablets can also contain disintegrators. Disintegrators are substances that swell when wetted to break up the tablet and release the compound. They include starches, clays, celluloses, algins, and gums. As further illustration, corn and potato starches, methylcellulose, agar, bentonite, wood cellulose, powdered natural sponge, cation-exchange resins, alginic acid, guar gum, citrus pulp, sodium lauryl sulfate, and carboxymethylcellulose can be used.

Compositions can be formulated as enteric formulations, for example, to protect the active ingredient from the strongly acid contents of the stomach. Such formulations can be created by coating a solid dosage form with a film of a polymer which is insoluble in acid environments and soluble in basic environments. Illustrative films include cellulose acetate phthalate, polyvinyl acetate phthalate, hydroxypropyl methylcellulose phthalate, and hydroxypropyl methylcellulose acetate succinate.

When it is desired to administer the compound as a suppository, conventional bases can be used. Illustratively, cocoa butter is a traditional suppository base. The cocoa butter can be modified by addition of waxes to raise its melting point slightly. Water-miscible suppository bases, such as polyethylene glycols of various molecular weights, can also be used in suppository formulations.

Transdermal patches can also be used to deliver the compounds. Transdermal patches can include a resinous composition in which the compound will dissolve or partially dissolve; and a film which protects the composition and which holds the resinous composition in contact with the skin. Other, more complicated patch compositions can also be used, such as those having a membrane pierced with a plurality of pores through which the drugs are pumped by osmotic action.

As one skilled in the art will appreciate, suitable formulations include those that are suitable for more than one route of administration. For example, the formulation can be one that is suitable for both intrathecal and intracerebral administration. Alternatively, suitable formulations include those that are suitable for only one route of administration as well as those that are suitable for one or more routes of administration, but not suitable for one or more other routes of administration. For example, the formulation can be one that is suitable for oral, transdermal, percutaneous, intravenous, intramuscular, intranasal, buccal, and/or intrathecal administration but not suitable for intracerebral administration.

As one skilled in the art will also appreciate, the formulation can be prepared with materials (e.g., actives excipients, carriers, diluents, etc.) having properties (e.g., purity) that render the formulation suitable for administration to humans. Alternatively, the formulation can be prepared with materials having purity and/or other properties that render the formulation suitable for administration to non-human subjects, but not suitable for administration to humans.

The following list of formulations is illustrative. These illustrative formulations may be suitable for preparing pharmaceutical compositions that include compounds which induce polyploidization of megakaryocytes as "active ingredients." The following list of formulations is illustrative and should not be interpreted as limiting the present disclosure or claims in any way:

Formulation 1
Hard gelatin capsules may be prepared using the following ingredients:

|  | Quantity (mg/capsule) |
| --- | --- |
| Active Ingredient | 250 |
| Starch, dried | 200 |
| Magnesium stearate | 10 |
| Total | 460 mg |

The above ingredients are mixed and filled into hard gelatin capsules in 460 mg quantities.

Formulation 2

|  | Quantity (mg/tablet) |
| --- | --- |
| Active Ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3
An aerosol solution may be prepared containing the following components:

|  | Weight % |
| --- | --- |
| Active Ingredient | 0.25 |
| Ethanol | 29.75 |
| Propellant 22 (chlorodifluoromethane) | 70.00 |
| Total | 100.00 |

The active compound is mixed with ethanol and the mixture added to a portion of the Propellant 22, cooled to −30° C. and transferred to a filling device. The required amount is then fed to a stainless steel container and diluted with the remainder of the propellant. The valve units are then fitted to the container.

Formulation 4
Tablets each containing 60 mg of active ingredient may be made as follows:

| Active Ingredient | 60 mg |
| --- | --- |
| Starch | 45 mg |
| Microcrystalline cellulose | 35 mg |
| Polyvinylpyrrolidone | 4 mg |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate, and talc, previously passed through a No. 60 mesh U.S. sieve, are then added to the granules which, after mixing, are compressed on a tablet machine to yield tablets each weighing 150 mg.

Formulation 5
Capsules, each containing 80 mg medicament may be made as follows:

| Active Ingredient | 80 mg |
| --- | --- |
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 sieve, and filled into hard gelatin capsules in 200 mg quantities.

Formulation 6
Suppositories each containing 225 mg of active ingredient may be made as follows:

| Active Ingredient | 225 mg |
| --- | --- |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions each containing 50 mg of medicament per 5 ml dose may be made as follows:

| | |
|---|---|
| Active Ingredient | 50 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The medicament is passed through a No. 45 mesh U.S. sieve and mixed with the sodium carboxymethyl, cellulose and syrup to form a smooth paste. The benzoic acid solution, flavor, and color are diluted with some of the water and added with stirring. Sufficient water is then added to produce the required volume.

Formulation 8

An intravenous formulation containing 100 mg of medicament per 5 ml dose may be prepared as follows:

| | |
|---|---|
| Active Ingredient | 100 mg |
| Mannitol | 100 mg |
| 5 N Sodium hydroxide | 200 ml |
| Purified water to total | 5 ml |

EXAMPLE

The following examples are illustrative and are not intended to limit the disclosed subject matter.

Example 1

Abstract

Leukemia develops when blood cell precursors grow excessively. There are many different forms of leukemia, which are classified by the type of blood cell that is affected or by the genetic abnormality that causes the disease. Unfortunately, there is no one treatment that works for all types, and in general, the most effective therapies are specifically targeted to the molecular causes of each disease. One very aggressive form of blood cancer for which there are few promising treatment options is Acute Megakaryocytic Leukemia (AMKL). This malignancy, which is generally fatal within one year of diagnosis, is caused by the uncontrolled growth of megakaryocytes, the cells that release platelets into the bloodstream to control bleeding. Here, it is proposed to develop novel therapeutics for leukemias such as AMKL.

Specific Aim and Rationale

Acute Megakaryocytic Leukemia (AMKL) is an aggressive and largely fatal hematologic malignancy. With the exception of individuals with Down syndrome, the long-term prognosis of AMKL patients is dismal, with an average survival of only eight months. Clearly, new, targeted therapies are needed. Here, novel therapies for AMKL are proposed.

Rationale

Although rare, megakaryocytic leukemia is an aggressive and deadly form of cancer that, in general, does not respond to current treatment regimens. Several recent clinical studies have highlighted the need for research in this area. Barnard and colleagues, in their study of pediatric patients enrolled on the Children's Oncology Group (COG) A2891 trial, concluded that: " . . . a greater understanding of the pathophysiology of childhood MDS, M6 and M7 is needed so that more effective therapies can be designed"(1). Similarly, Tallman and colleagues, in their report on outcomes of adults with AMKL in the Eastern Cooperative Oncology Group (ECOG) study, stated: "Although half of the [AMKL] patients achieved CR [complete remission], the long-term outcome is extremely poor, primarily attributable to resistant disease. New therapeutic strategies are needed"(2). Finally, Pagano and colleagues, in a report of GIMEMA European trials concluded: "The CR duration and the overall survival in this group of [AMKL] patients are very poor, even if similar to those observed in other AML. Furthermore, a high number of deaths in CR were observed. On the basis of these data, a specific therapeutic approach, possibly with innovative treatments, should be evaluated"(3). These reports provide strong rationale for research aimed at identifying new treatments for megakaryocytic leukemia. In this application, three related aims are proposed to increase an understanding of AMKL and to develop targeted therapeutics. It is believed that this combination of basic and translational research will facilitate the development of these new agents.

Background

Megakaryocyte Biology

Megakaryocytes (MKs) arise from the Megakaryocyte-Erythroid Progenitor (MEP) and progress through discrete maturation stages (FIG. 1). Committed megakaryocyte progenitors, including the colony-forming unit megakaryocyte (CFU-MK), proliferate to a limited extent, giving rise to megakaryoblasts. Individual cells then undergo terminal differentiation and eventually shed platelets. In concert with cytoplasmic maturation that leads to platelet production, megakaryocyte nuclei undergo a maturation process that involves repeated rounds of DNA synthesis without cell division, a variant cell cycle termed polyploidization, or endomitosis (4). This phenomenon allows megakaryocytes to accumulate DNA content up to 64N and greatly increases their size and protein production. These increases in cell size, DNA content, and protein levels are associated with the development of long cytoplasmic extensions, termed pro-platelet, which eventually shed platelets.

Megakaryocytic Diseases

Disorders that are characterized by aberrant megakaryopoiesis include acute megakaryocytic leukemia (AMKL), essential thrombocythemia (ET), and primary myelofibrosis (PMF).

AMKL: This is a rare, but aggressive myeloid leukemia that affects three groups of patients: children with DS (DS-AMKL), infants without Down syndrome (non-DS pediatric AMKL), and adults. AMKL comprises approximately 5-7% of AML in children without DS and approximately 1% of adult AML (for review, see (5)). In the context of DS, however, megakaryocytic disorders are relatively common, occurring in at least 10% of newborns (6). Each of these AMKL subtypes has unique clinical and genetic features. i) DS-AMKL blasts harbor mutations in GATA1 that block expression of the full-length protein, but allow for expression of a shorter isoform named GATA-1s. It is hypothesized that the combination of trisomy 21 and a GATA1 mutation contribute to initiation of the disease, but that additional genetic mutations are needed for the evolution to acute leukemia (7). Although, the current treatment regimen has resulted in favorable outcomes for this group of patients, with an overall survival of 77% at 5 years (8), 10-20% of children with DS-AMKL die from this leukemia and/or from the toxicity of the treatment. ii) Many infant cases of non-DS AMKL are associated with the (1:22) translocation, which was initially discovered in 1991 and recently found to result in fusion of the RBM15 and MKL1 genes (5). In other cases of childhood non-DS AMKL, different cytogenetic abnormalities are observed, including t(10;11), t(9;11), +8 or +21 (5). Of note, all groups of children with non-DS AMKL show significantly inferior overall survival and event free survival compared to children diagnosed with other myeloid leukemias (FAB M0-M5) or with DS-AMKL (5). iii) Much less is known about the etiology of adult AMKL, as no specific chromosomal rearrangements or genetic mutations have been described, apart from rare detection of mutations in JAK2 or JAK3 (5, 9). Although some patients achieve complete remission, the long-term outcome is significantly worse for AMKL than other forms of adult AML, with a median survival of 40 weeks or less (2). In summary, new therapeutics are desperately needed for this leukemia.

PMF, PV, and ET: These myeloproliferative diseases are characterized by an abnormal expansion of megakaryocytes or erythroid progenitors that can differentiate. Due to high platelet counts, patients with ET are at significantly increased risk of thrombotic events. PMF patients suffer from cytopenias that result from bone marrow fibrosis and also show a risk of evolving to AML. Recent molecular studies have shown that JAK2 mutations are found in nearly half of ET patients and >95% individuals with PV, while JAK2 and c-MPL mutations account for 30-50% and 10% of PMF cases, respectively (10). This discovery has fueled the development of a new generation of JAK2 inhibitors, which appear to alleviate some symptoms of the disease, but are not curative.

Development of Targeted Therapies for AMKL

The paradigm for successful, targeted differentiation therapy is the use of all trans retinoic acid (ATRA) for treatment of Acute Promyelocytic Leukemia (APL) (for a review, see (20). Prior to the development of ATRA therapy, the prognosis for patients with APL, which represents 5-10% of adult AML, was very poor. In contrast, the vast majority of APL patients treated with ATRA achieve hematologic remission (21-23). One aim of the current study is to test novel therapeutic strategies for AMKL, in particular, whether the forced induction of MK polyploidization can serve as a "differentiation therapy" for AMKL. Promoting polyploidization is attractive as a differentiation therapy, because the commitment to polyploidization is linked to cessation of proliferation. Preliminary data show that SU6656, a Src kinase inhibitor that can initiate MK polyploidization, effectively reduces proliferation of both wild-type and GATA-1 mutant megakaryocyte progenitors, indicating that this approach can override the effects of genetic alterations. Furthermore, megakaryocytes are one of the few cell types that are poised to undergo polyploidization during normal maturation. This may suggest that they will be more sensitive to these agents than other cell types, providing a therapeutic window for specifically targeting AMKL.

Research Methods

Assessing Small Molecule Inducers of MK Polyploidization as Differentiation Therapeutics for AMKL Rationale: AMKL is an aggressive and deadly form of cancer that, in general, does not respond to current treatments. Molecules that modulate the shift from proliferation to polyploidization of megakaryocyte precursors may represent novel therapeutic agents for this disease as well as ET and PMF.

Preliminary Data:

Inhibition of Src Kinases Induces Polyploidization

To study how megakaryocytes switch from a proliferative to endomitotic cell cycle, the Src kinase inhibitor SU6656 is being utilized. SU6656 has previously been reported to promote polyploidization of megakaryocytes (32). As shown in FIG. 2, SU6656 is shown to promote polyploidization of both human and mouse megakaryocytic cell lines, including Y10, GIME and CMK cells, as well as primary murine megakaryocytes (FIG. 2 A,B,C and data not shown). Of note, SU6656 efficiently promoted polyploidization of wild-type (Y10), GATA1-null (GIME) and GATA1/JAK3 double mutant megakaryocytes (the CMK cell line). In experiments, the induction of endomitosis was linked to cessation of proliferation (FIG. 2D), suggesting that inducing polyploidization forces exit from the proliferative cell cycle and may thus serve as a novel therapy for AMKL.

Figure 3A:
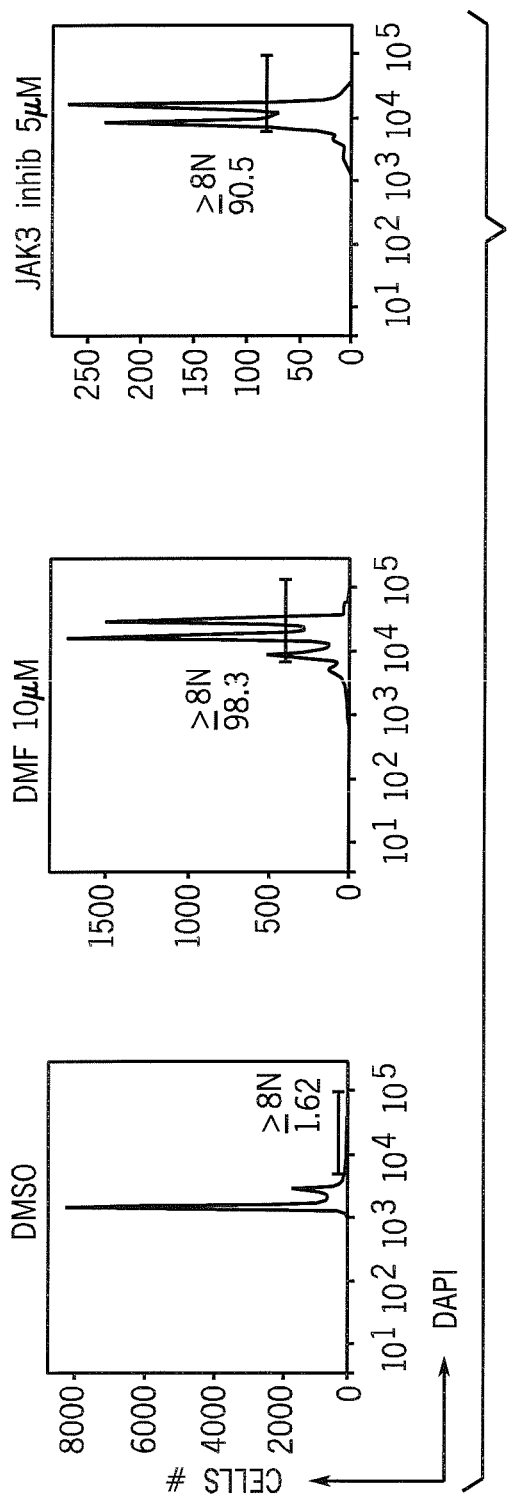
FIG. 3 illustrates that DMF and JAK3 inhibitor (VI) are potent inducers of GIME cell polyploidization and that DMF also induces megakaryocyte differentiation. a) GIME cells were cultured with DMSO, DMF or JAK3 inhibitor for 48 hours, fixed and stained with DAPI. DNA content was then assessed by flow cytometry. Numbers above the bar indicate % of cells ≥8N. b) After 48 hours, GIME cells from a) were stained with anti-CD42 antibodies and the cell surface expression of CD42 was evaluated by flow cytometry.
Figure 3B:
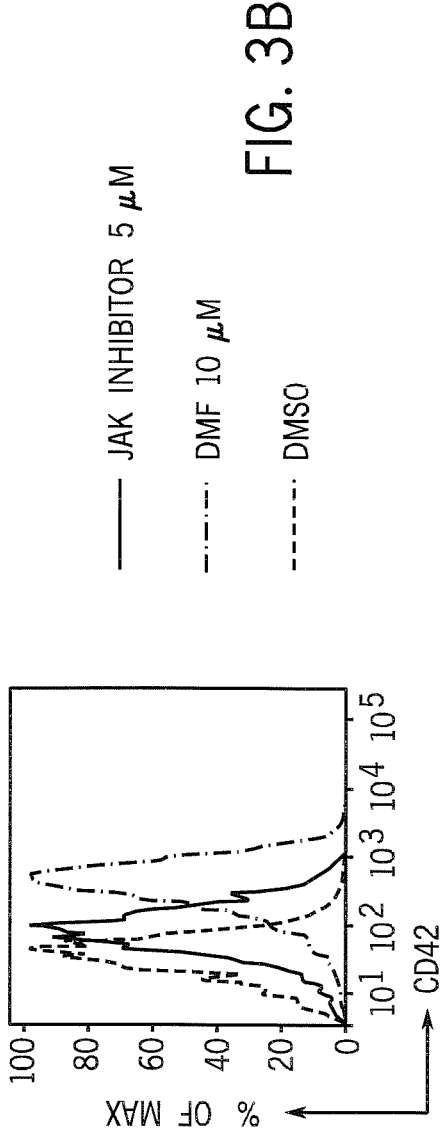
Figure 4:
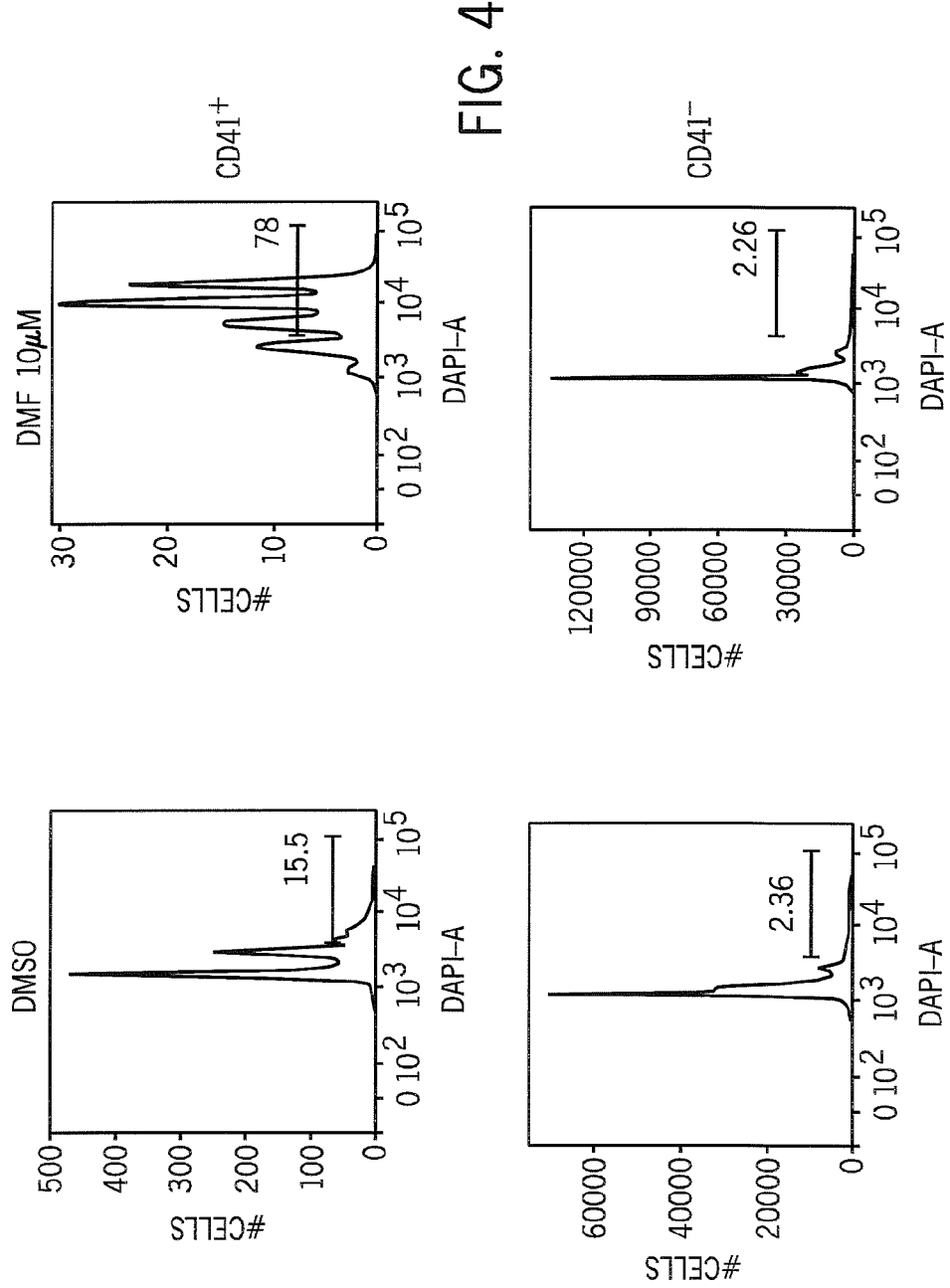
FIG. 4 illustrates that DMF induces polyploidization of normal human megakaryocytes and that its activity is restricted to the CD41+ population. Human CD34+ cells were cultured with TPO for 12 days and then fixed and stained with DAPI. DMSO or DMF were added to the culture after 9 days. DNA content was then assessed by flow cytometry. Numbers above the bar indicate % of cells ≥8N.

High throughput Screen to Identify Novel and Specific Inducers of MK Polyploidization Although SU6656 has a fairly robust ability to promote MK polyploidization, it has similar effect on other non-MK cell types. In collaboration with the Broad Institute, a high throughput screen for small molecules was conducted to identify small molecules that preferentially induce polyploidization or differentiation of megakaryocytes. We screened 10,000 compounds from the Broad's extensive collection of small molecules (including known bioactives, kinase and HDAC inhibitors, and natural products) to identify inducers of megakaryocyte polyploidization. The screen was performed in the following manner: 1) 4,000 CMK (human megakaryocytic leukemia) cells were plated into each well of a 384-well plate, 2) 100 nl of compounds (yielding a final concentration of 10 µM) were pinned into the wells, 3) plates were incubated at 37° C. for 72 hours, 4) cells were fixed and stained with Hoescht, and 5) plates were imaged using an ImageXpressMICRO high content imager with 20× objective. Nine images per well were collected. 6) Data were analyzed using both MetaXpress software and "Cell Profiler," software designed at MIT and the Broad Institute. Seventy-two plates containing duplicates of nearly 10,000 small molecules were screened. In preliminary analysis of the screening data, 206 positive compounds (a hit rate of 2.06%) were identified. This group of positives includes the expected classes of microtubule disrupting and stabilizing agents, actin disrupting agents, and SU6656. More interestingly, this initial group is comprised of other bioactive molecules, including DMF, a Rho-kinase (ROCK) inhibitor. Interestingly, a recent report by Shivdasani's group has shown that ROCK inhibition facilitates pro-platelet formation (33) suggesting that this agent may facilitate differentiation in addition to polyploidization. We have confirmed that the Rho-kinase inhibitor identified in the Broad screen is a potent inducer of polyploidization of a panel of MK cell lines, including CMK, Meg-01 and GIME (FIG. 3 and data not shown). The Rho-kinase inhibitor (DMF) induced robust differentiation as evidenced by the expression of the late megakaryocyte marker CD42 as analyzed by flow cytometry (FIG. 3, DMSO (0.3%); JAK inhibitor 5 µM (7.0%); DMF 10 µM (66.3%)). Furthermore, this Rho-kinase inhibitor potently induced polyploidization of primary human megakaryocytes, but had no effect on the growth of non-megakaryocytic bone marrow cells (FIG. 4). These results show that the Rho-kinase inhibitor (DMF) induced robust polyploidization of the CD41+ megakaryocyte fraction, but had no effect on the non-megakaryocytic cells (CD41-negative) population (FIG. 4). Thus, this small molecule appears to be a potent and selective inducer of MK polyploidization. This molecule and another lead compound have been tested as discussed below.

Experimental Approach:

i) Validating Lead Compounds

Lead compounds were tested for their activity and specificity in follow-up studies using cell lines and primary cells. In particular, compounds that preferentially promote polyploidization of megakaryocytes as opposed to other cell types were sought. In conjunction with the Broad Institute, validation studies were performed by incubating CMK cells with titrations of the 206 lead compounds. In addition, these assays were expanded to test these lead compounds on other MK cell lines, including GIME and Meg-01, and on two non-MK cell lines, Jurkat and 293 cells. After this round of screening, several potent and specific inducers of MK polyploidization were identified.

ii) Testing Lead Compounds on Human AMKL Specimens

The most promising small molecules were tested on the growth and survival of primary human AMKL specimens (obtained through collaboration with ECOG). The procedures and results are discussed below.

iii) Evaluate whether Polyploidization Inducers Interfere with Development of AMKL In Vivo in 6133/MPL Transplant Model To determine whether polyploidization-inducing agents can serve as new therapies for AMKL, we established an AMKL animal model. We developed an animal model of AMKL by transplanting 6133/MPL megakaryocytic leukemia cells (35) into sub-lethally irradiated recipient C57Bl/6 mice. The parental 6133 cell line, which is dependent upon TPO for survival, was derived from a leukemic mouse that expressed the AMKL t(1:22) fusion protein OTT-MAL by knock-in gene targeting. 6133 cells were then transduced with a MPLW515L expressing retrovirus, and stable TPO-independent clones were isolated. We discovered that C57Bl/6 mice transplanted with 1 million 6133/MPL cells developed a fulminant AMKL within 21 days. The disease was characterized by massive infiltration of CD41+ cells in the bone marrow and spleen. These mice will be utilized as animal models to quantify the effect of small molecule inducers of polyploidization on disease progression in vivo.

Alternative Approaches/Future Studies

In most cases, lead compounds are commercially available. In other cases, the compounds may be synthesized (e.g., by chemists at the Broad Institute). One long-term goal is to develop clinical trials for small molecule inducers of polyploidization. Separately, in addition, to pursuing these small molecules as novel therapeutics for AMKL, ET, and PMF, these small molecules also will be utilized as tools to increase an understanding of the regulation of polyploidization of normal MKs. For example, targets of these small molecules may be identified. For these latter studies, proteomic approaches similar to those used by Stegmaier and colleagues at the Broad Institute (34) as well as RNAi based approaches may be utilized.

Example 2

Results

Figure 5:
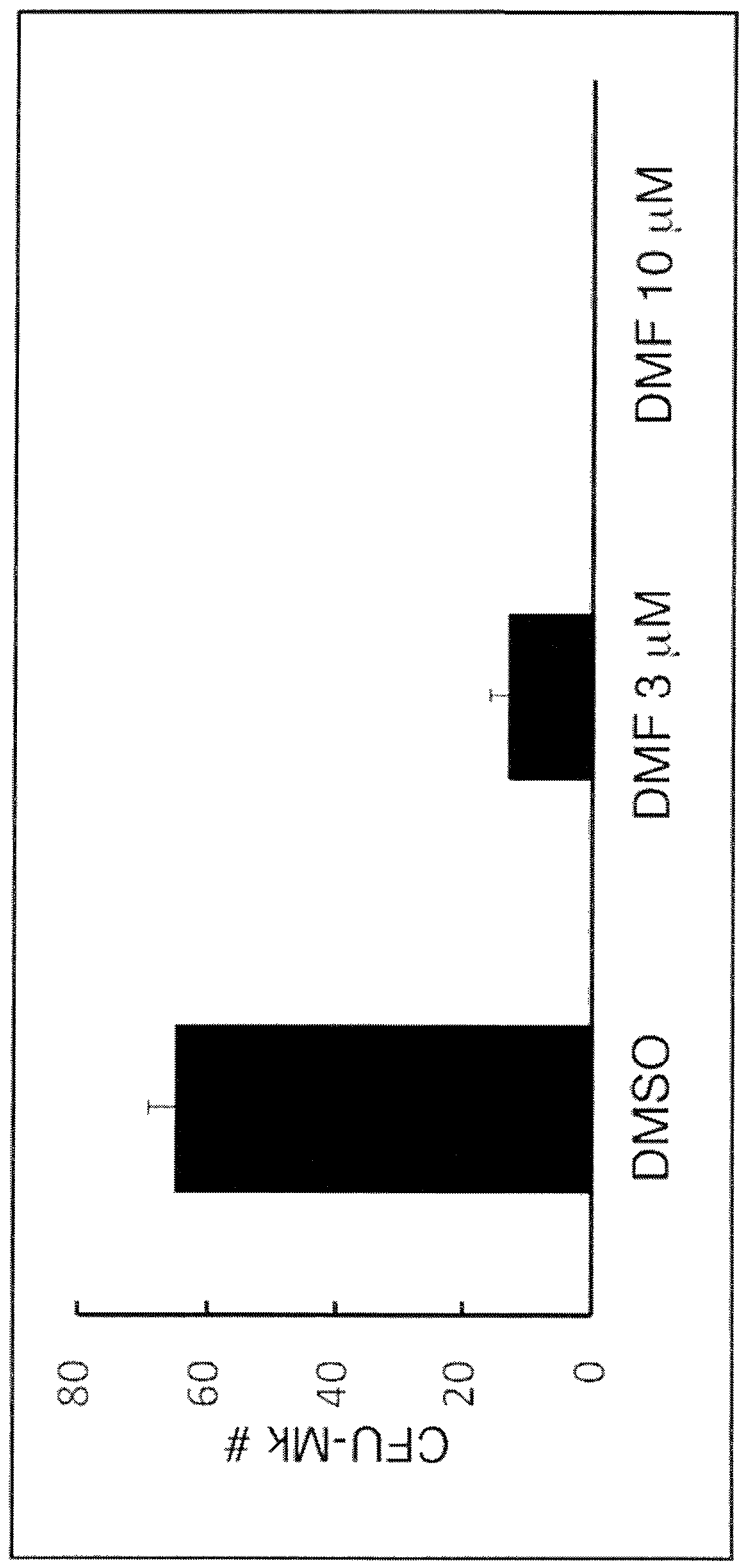
FIG. 5 illustrates that the Rho kinase inhibitor dimethylfasudil (DMF) (also know as "ROCK inhibitor") blocks formation of megakaryocyte colonies (CFU-MK) by bone marrow from patients with Myeloproliferative Disease (MPD).
Figure 6:
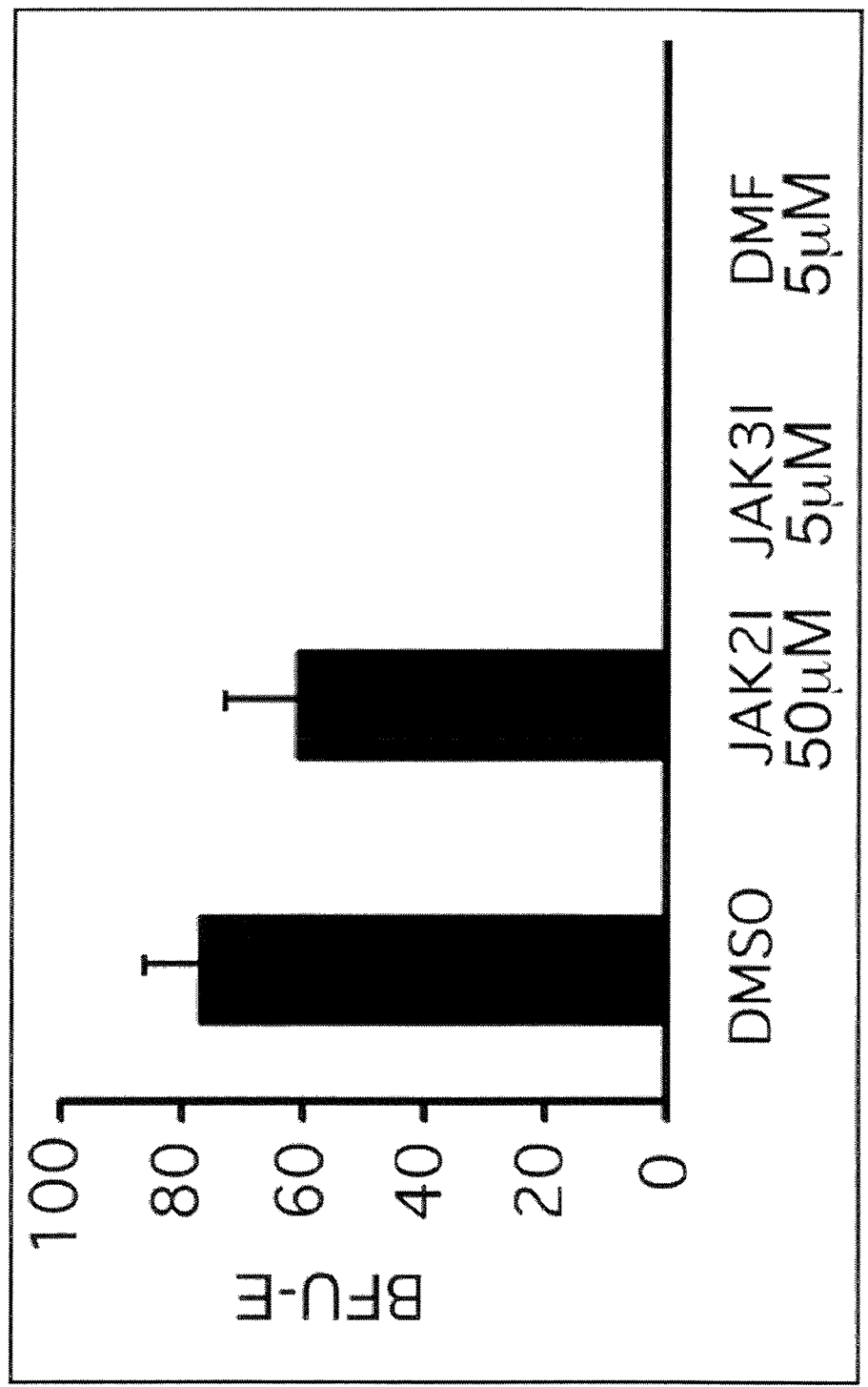
FIG. 6 illustrates that dimethylfasudil and JAK3 inhibitor VI (JAK3I) block formation of erythroid colonies in human MPD bone marrow cultures.
Figure 7:
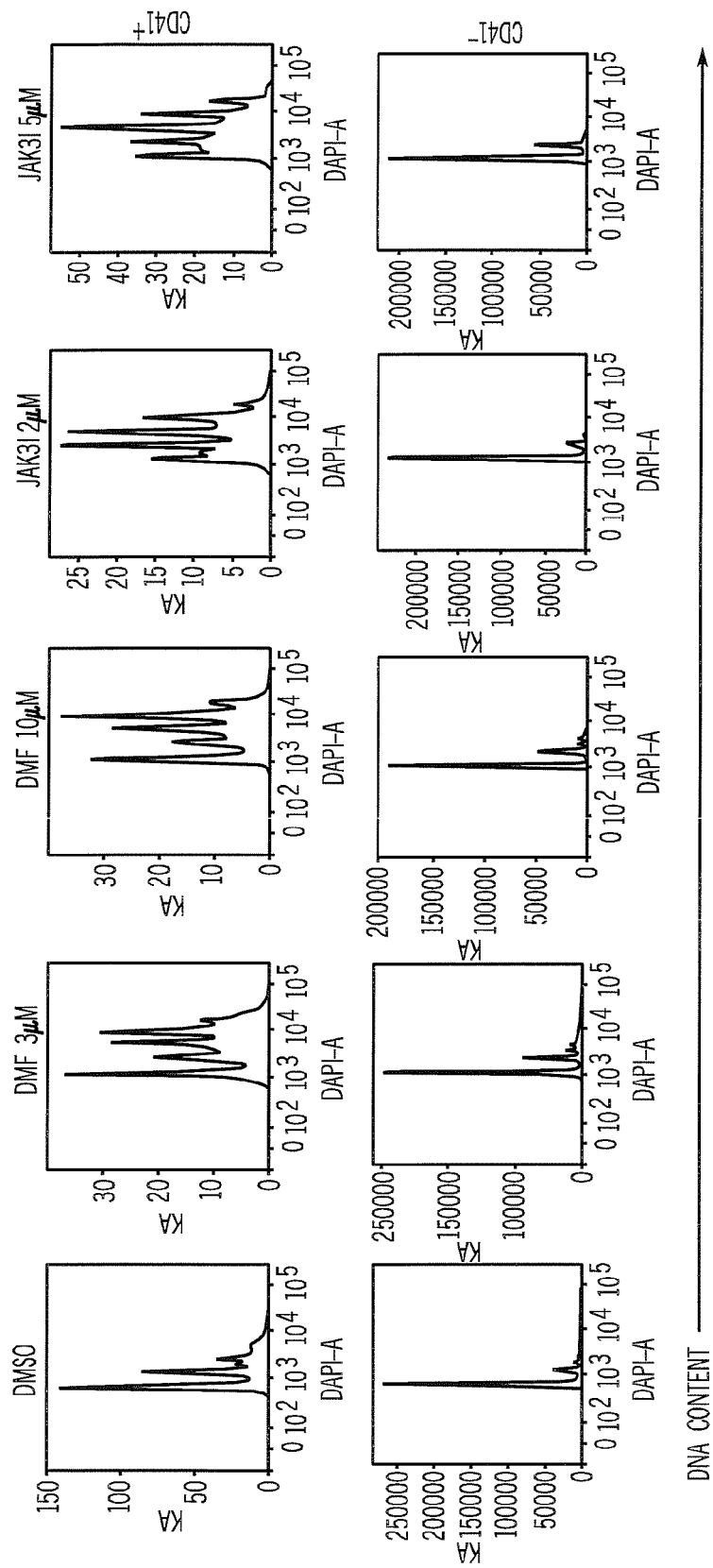
FIG. 7 illustrates that DMF and JAK3 inhibitor induce polyploidization of CD41+ megakaryocytes obtained from human MPD bone marrow.
Figure 8:
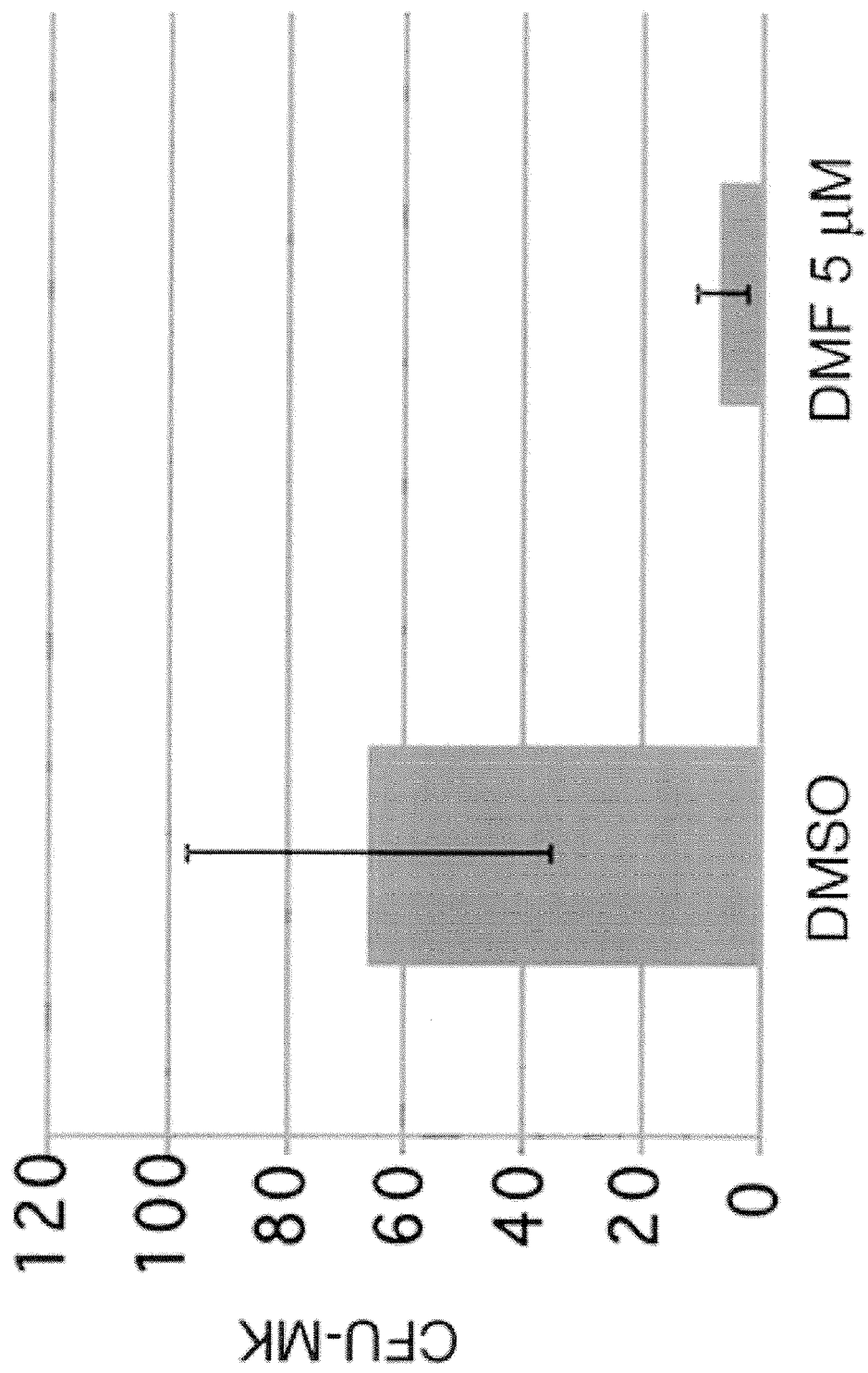
FIG. 8 illustrates that DMF blocks the growth of human AMKL leukemic cells. Mononuclear cells from patients with AMKL were cultured in methylcellulose in the presence of either DMSO or 5 µM of DMF.

Data with Patient Samples. Two lead compounds were tested on samples from both MPD (myeloproliferative disease) patients and AMKL (acute megakaryocytic leukemia) patients. The lead compounds included dimethylfasudil (DMF, also known as "Rho kinase inhibitor") and JAK3 inhibitor VI (JAK3I). Referring to FIG. 5, bone marrow mononuclear cells from a patient with ET were cultured with two doses of DMF for 10 days. DMF potently blocked formation of aberrant megakaryocyte colonies. Referring to FIG. 6, bone marrow mononuclear cells from a patient with ET were cultured with DMF, a JAK2 inhibitor, JAK3 inhibitor VI, or DMSO for 14 days. DMF and JAK3 inhibitor VI potently blocked formation of aberrant erythroid colonies. Referring to FIG. 7, DMF and JAK3 inhibitor both potently induced polyploidization of bone marrow megakaryocytes from a patient with ET. The two drugs selectively induce polyploidization of the CD41-population (representative of megakaryocytes), but have no effect on CD41-cells (all other cell types). These results highlight the utility of the agents in selectively preventing the growth of MPD cells. Referring to FIG. 8, bone marrow samples from patients with AMKL were cultured in DMSO (control) or DMF (at 5 µM) for 14 days. Colonies were stained with anti-CD41 antibody and visualized by microcopy (not shown). Total numbers of CD41+ megakaryocyte colonies are shown. DMF potently blocked growth of the human leukemia cells.

Animal Models. DMF was shown to significantly block progression of AMKL in mice in two ways. A) Pre-treatment of AMKL cells with DMF interfered with their ability to cause a tumor in recipient mice. B) Feeding DMF to mice blocked tumor development and lead to long-term survival of up to 50% of the mice.

To determine whether polyploidization-inducing agents can serve as new therapies for AMKL, DMF was assessed in an animal model for AMKL. To this end, an animal model of AMKL was developed by transplanting 6133/MPL megakaryocytic leukemia cells into sub-lethally irradiated recipient C57Bl/6 mice. The parental 6133 cell line, which is dependent upon TPO for survival, was derived from a leukemic mouse that expressed the AMKL t(1:22) fusion protein OTT-MAL by knock-in gene targeting (35). 6133 cells were then transduced with a MPLW515L expressing retrovirus, and stable TPO-independent clones were isolated. C57Bl/6 mice transplanted with 1 million 6133/MPL cells were observed to develop a fulminant AMKL within 21 days. The disease was characterized by massive infiltration of CD41$^+$ cells in the bone marrow and spleen.

Figure 9:
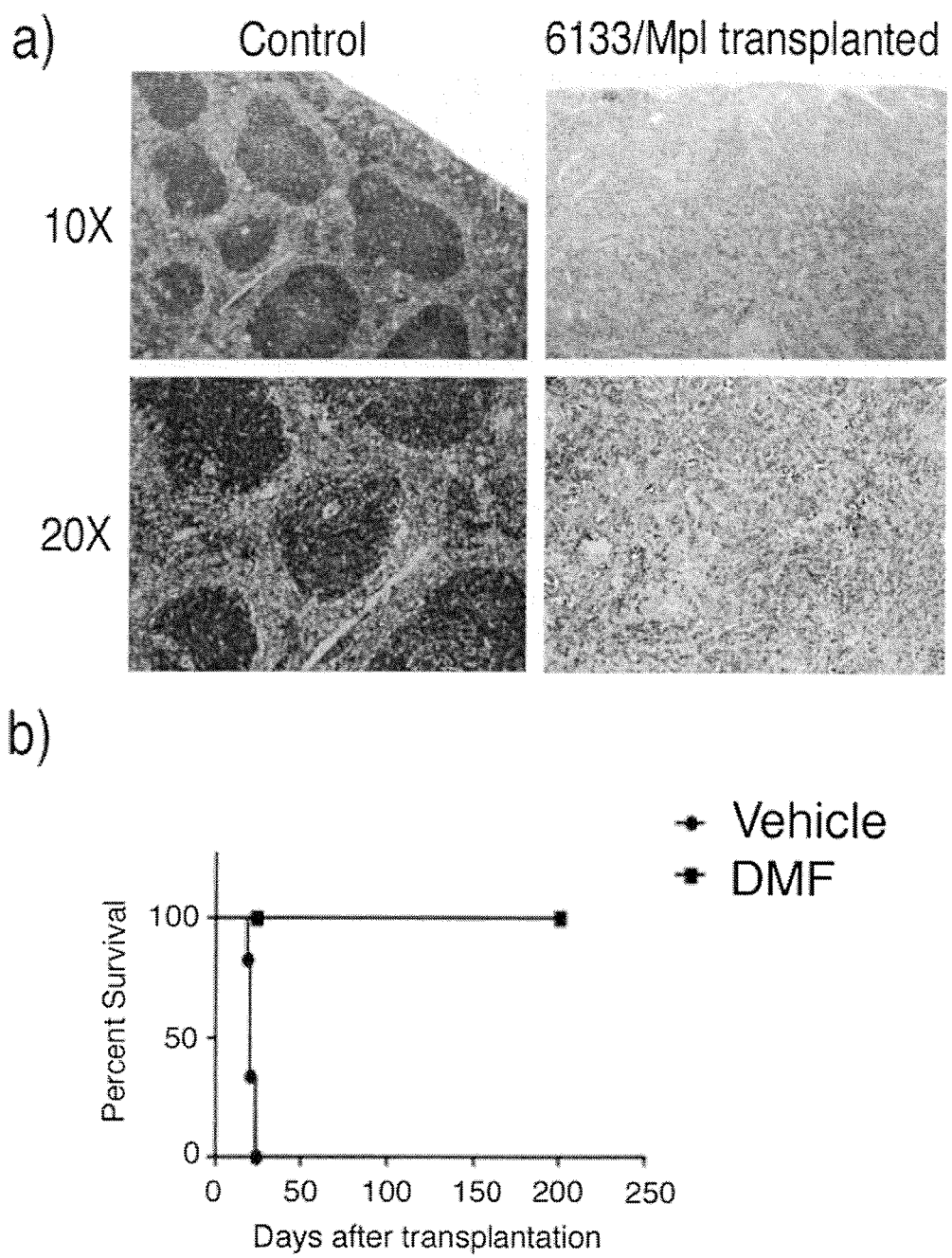
FIG. 9 illustrates that DMF blocks the development of AMKL in vivo. a) Histology of spleens from control and 6133/MPL transplanted mice at 20 days. b) Survival analysis of the effect of DMF pre-treatment on AMKL development in recipient mice. p<0.0005 (Log rank test). N=6 mice (vehicle (DMSO) pre-treatment) or N=7 (DMF pre-treatment) per group.

To determine whether DMF could prevent AMKL in this transplant model, 6133/MPL cells were pre-treated with DMSO or 5 µM DMF for 24 hours. Viable mononuclear cells were collected by separation with Ficoll, and then 1 million of these viable cells were transplanted into sub-lethally irradiated C57Bl/6 mice. Six control mice and seven DMF pre-treated mice were included in each group. Whereas pre-treatment with DMSO had no effect on leukemia development, with all animals developing a fulminant AMKL within 22 days, pre-treatment with DMF led to a striking and significant delay in progression of AMKL (FIG. 9). In fact, all of the mice implanted with DMF-pretreated cells are healthy and show no signs of disease (for at least 200 days). Thus, DMF shows tremendous potential as a novel therapy for AMKL.

Figure 10:
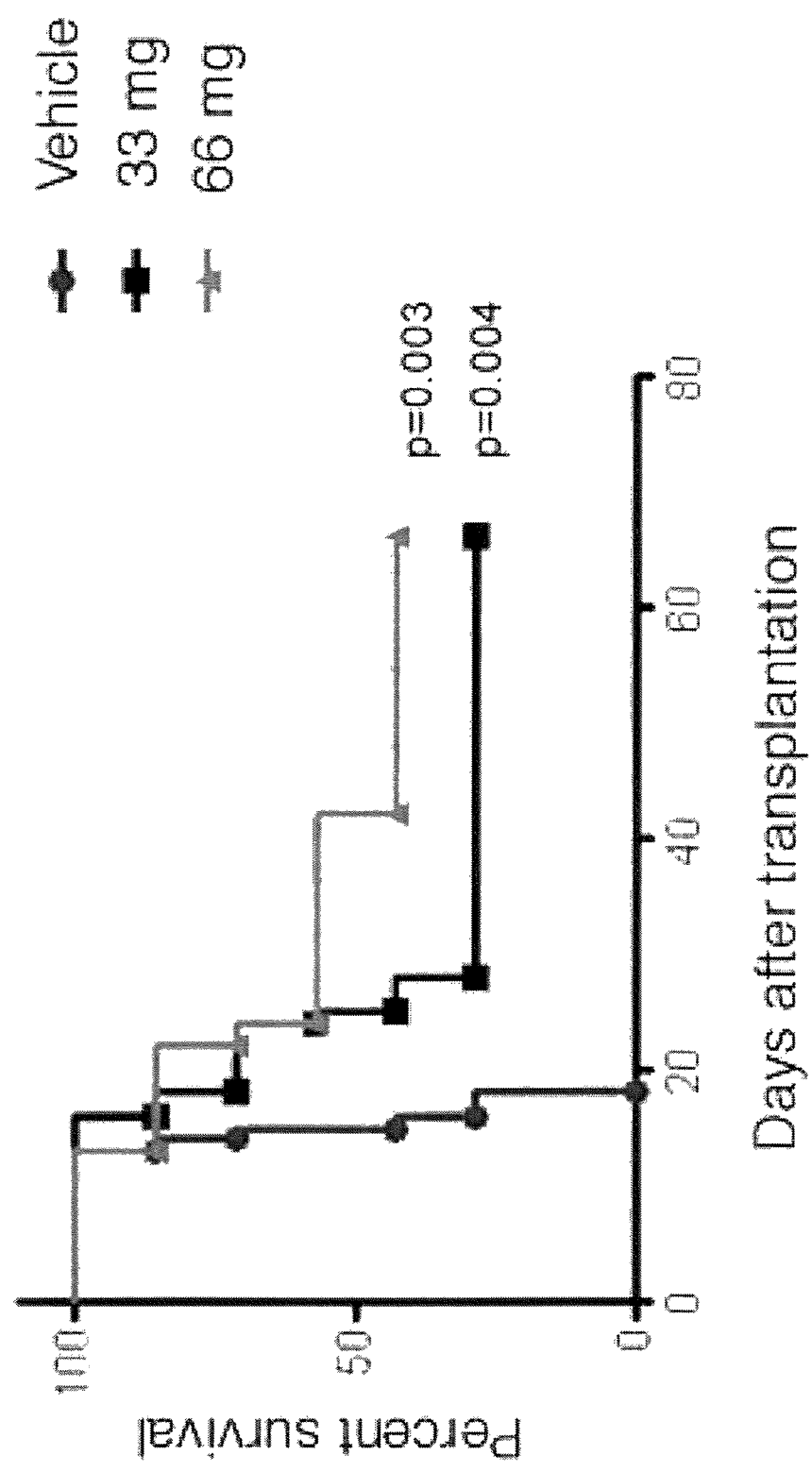
FIG. 10 illustrates that DMF prevents AMKL in vivo. N=7 per group. 6133/MAL transplant recipients were treated with two daily doses of vehicle, 33 mg/kg DMF, or 66 mg/kg DMF by oral gavage. Treatment with 33 or 66 mg/kg DMF led to statistically significant extensions in leukemia free survival (p=0.003 and 0.004 respectively).

To show that DMF can also prevent leukemia when fed to mice, 1 million 6133/MPL cells were transplanted into recipient C57Bl/6 mice. After 3 days, the mice were treated with twice daily doses of DMF for 10 days. Seven mice were utilized per experimental condition. Treatment with either 33 mg/kg or 66 mg/kg led to significant extensions in lifespan (FIG. 10). With 66 mg/kg nearly 50% of the mice remained disease free for at least 70 days. In contrast, all of mice fed only water (vehicle) died of leukemia by 20 days. This experiment shows that DMF can cure AMKL in a mouse model.

Methods

Patient Samples and Colony Forming Assay

AMKL Patient Specimens. Frozen bone marrow mononuclear cells of acute megakaryocytic leukemia (AMKL) were obtained from human patients with help from the Children's Oncology Group (COG). After thawing, cells were resuspended in IMDM media without serum. The cells were stained with 0.4% trypan blue solution for 5 minutes and live cells were counted. Live cells were assayed for leukemic potential in a CFU-MK assay (details below).

MPDs Patient Specimens. Mononuclear cells from bone marrow of patients were obtained by informed consent from patients at Northwestern Feinberg School of Medicine. Mononuclear cells were separated from marrow with Ficoll (GE Healthcare life sciences, Piscataway, N.J.) and resuspended in IMDM (Iscove's Modified Dulbecco's Media) media without serum. The cells were stained with 0.4% trypan blue solution for 5 minutes and live cells were counted. Live cells were assayed in CFU-MK ("Colony forming units-megakaryocytes") and BFU-E ("Burst forming unit-erythroid") assays as well as in liquid culture.

CFU-MK (Colony forming units-megakarvocvtes) assay. Live cells were added to Mega-Cult C media (4901, StemCell Technologies, Vancouver, BC, Canada) with recombinant human TPO (thrombopoeitin, 50 ng/ml), recombinant human IL-6 (10 ng/ml), and recombinant human IL-3 (10 ng/ml). DMF or DMSO was added to Mega-Cult C media. Cells were plated in duplicate chamber slides according the manufacturer's protocol. After 10 days, the chamber slides were fixed, and stained with anti-human CD41 antibody. Slides were scored microscopically, and megakaryocyte colonies were defined as colonies with at least three megakaryocytes.

BFU-E (Burst forming unit-erythroid) assay. Live ET bone marrow cells were added to MethoCult media (4436, StemCell Technologies, Vancouver, BC, Canada) with recombinant human EPO (erythropoeitin, 3 U/mL), recombinant human SCF (stem cell factor, 50 ng/mL), recombinant human GM-CSF (granulocyte macrophage colony-stimulating factor, 10 ng/mL) and recombinant human IL-3 (10 ng/mL). DMF, JAK3 inhibitor VI or DMSO was added to MethoCult media. Cells were plated in duplicate in 35 mm culture dishes according the manufacturer's protocol. On the $14^{th}$ day, red colonies composed of hemoglobinized erythroblasts were identified and scored.

Liquid culture. Marrow cells from ET patients were also cultured in RPMI with 10% FBS in the presence of recombinant human TPO (thrombopoeitin, 50 ng/ml). Cells were incubated with different concentration of DMF, JAK3 inhibitor VI or DMSO. After 5 days, the cells were collected and stained with APC (allophycocyanin) labeled anti-human CD41 antibody (BD Biosciences San Jose, Calif.). The cells were then stained overnight with 1 μg/mL 4',6-diamidinio-2-phenylindole (DAPI). DNA content of both CD41+ cells and CD41-negative cells was analyzed by utilizing a BD LSRII flow cytometer (BD Biosciences San Jose, Calif.).

Murine Model and Treatment with DMF

C57BL/6 mice (purchased from the Jackson Laboratory, Bar Harbor, Me.) were sub-lethally irradiated with 600 rads. Mice were then anesthetized by an IP injection of mixture of Ketamine (100 mg/kg) and xylazine (5 mg/kg) 2 hours after irradiation. C57/B16 mice were intravenously injected with $1\times10^6$ 6133/MPL cells, which were labeled with green fluorescent protein (GFP). Two different doses of DMF (33 mg/kg or 66 mg/kg) or water were administered to mice by oral gavage twice daily (b.i.d.) starting on the 3rd day after transplantation. For pre-treatment model, 6133/MPL cells were incubated with 5 μM DMF or DMSO for 24 hours. Live cells treated with DMF or water were separated with Ficoll and transplanted into sub-lethally irradiated mice. Development of disease was assessed with presence of GFP-positive cells in the peripheral blood by FACS and by monitoring the health and body weight of the animals. Mice were sacrificed based on a protocol that includes assessment of morbidity by >20% loss of weight, severe anemia, scruffy appearance, and/or severe lethargy.

REFERENCES

1. Barnard, D. R Alonzo, T. A., Gerbing, R. B., Lange, B. & Woods, W. G. (2006) Pediatr Blood Cancer.
2. Tallman, M. S., Neuberg, D., Bennett, J. M., Francois, C. J., Paietta, E., Wiernik, P. H., Dewald, G., Cassileth, P. A., Oken, M. M. & Rowe, J. M. (2000) Blood 96, 2405-11.
3. Pagano, L., Pulsoni, A., Vignetti, M., Mele, L., Fianchi, L., Petti, M. C., Mirto, S., Falcucci, P., Fazi, P., Broccia, G., Specchia, G., Di Raimondo, F., Pacilli, L., Leoni, P., Ladogana, S., Gallo, E., Venditti, A., Avanzi, G., Camera, A., Liso, V., Leone, G. & Mandelli, F. (2002) Leukemia 16, 1622-6.
4. Ravid, K., Lu, J., Zimmet, J. M. & Jones. M. R. (2002) J Cell Physiol 190, 7-20.
5. Wickrema, A. & Crispino, J. D. (2007) Oncogene 26, 6803-15.
6. Zipursky, A. (2003) Br J Haematol 120, 930-8.
7. Gurbuxani, S., Vyas, P. & Crispino, J. D. (2004) Blood 103, 399-406.
8. Al-Ahmari, A., Shah, N., Sung, L., Zipursky, A. & Hitzler, J. (2006) Br J Haematol 133, 646-8.
9. Walters, D. K., Mercher, T., Gu, T. L., O'Hare, T., Tyner, J. W., Loriaux, M., Goss, V. L., Lee, K. A., Eide, C. A., Wong, M. J., Stoffregen, E. P., McGreevey, L., Nardone, J., Moore, S. A., Crispino, J., Boggon, T. J., Heinrich, M. C., Deininger, M. W., Polakiewicz, R. D., Gilliland, D. G. & Druker, B. J. (2006) Cancer Cell 10, 65-75.
10. Levine, R. L. & Gilliland, D. G. (2007) Curr Opin Hematol 14, 43-7.
11. Shivdasani, R. A., Fujiwara, Y., McDevitt, M. A. & Orkin, S. H. (1997) Embo J 16, 3965-73.
12. Vyas, P., Ault, K., Jackson, C. W., Orkin, S. H. & Shivdasani, R. A. (1999) Blood 93, 2867-75.
13. Muntean, A. G. & Crispino, J. D. (2005) Blood 106, 1223-31.
14. Muntean, A. G., Pang, L., Poncz, M., Dowdy, S. F., Blobel, G. A. & Crispino, J. D. (2007) Blood 109, 5199-207.
15. Bourquin, J. P., Subramanian, A., Langebrake, C., Reinhardt, D., Bernard, O., Ballerini, P., Baruchel, A., Cave, H., Dastugue, N., Hasle, H., Kaspers, G. L., Lessard, M., Michaux, L., Vyas, P., van Wering, E., Zwaan, C. M., Golub, T. R. & Orkin, S. H. (2006) Proc Natl Acad Sci USA 103, 3339-44.
16. Wechsler, J., Greene, M., McDevitt, M. A., Anastasi, J., Karp, J. E., Le Beau, M. M. & Crispino, J. D. (2002) Nat Genet 32, 148-52.
17. Li, Z., Godinho, F. J., Klusmann, J. H., Garriga-Canut, M., Yu, C. & Orkin, S. H. (2005) Nat Genet 37, 613-9.
18. Rylski, M., Welch, J. J., Chen, Y. Y., Letting, D. L., Diehl, J. A., Chodosh, L. A Blobel, G. A. & Weiss, M. J. (2003) Mol Cell Biol 23, 5031-42.
19. Welch, J. J., Watts, J. A., Vakoc, C. R., Yao, Y., Wang, H., Hardison, R. C., Blobel, G. A., Chodosh, L. A. & Weiss, M. J. (2004) Blood 104, 3136-47.
20. Jing, Y. & Waxman, S. (2007) Curt Top Microbial Immunol 313, 245-69.

21. Huang, M. E., Ye, Y. C., Chen, S. R., Chai, J. R., Lu, J. X., Zhoa, L., Gu, L. J. & Wang, Z. Y. (1988) Blood 72, 567-72.
22. Warrell, R. P., Jr., Frankel, S. R., Miller, W. H., Jr., Scheinberg, D. A., Itri, L. M., Hittelman, W. N., Vyas, R., Andreeff, M., Tafuri, A., Jakubowski, A. & et al. (1991) N Engl J Med 324, 1385-93.
23. Dombret, H., Scrobohaci, M. L., Daniel, M. T., Miclea, J. M., Castaigne, S., Chomienne, C., Fenaux, P. & Degos, L. (1995) Leukemia 9, 19-24.
24. Horak, C. E., Mahajan, M. C., Luscombe, N. M., Gerstein, M., Weissman, S. M. & Snyder, M. (2002) Proc Natl Acad Sci USA 99. 2924-9.
25. Huang, Z., Richmond, T. D., Muntean, A. G., Barber, D. L., Weiss, M. J. & Crispino, J. D. (2007) J Clin Invest 117, 3890-9.
26. Jelinek, J., Oki, Y., Gharibyan, V., Bueso-Ramos, C., Prchal, J. T., Verstovsek, S., Beran, M., Estey, E., Kantarjian, H. M. & Issa, J. P. (2005) Blood 106, 3370-3.
27. Steensma, D. P., McClure, R. F., Karp, J. E., Tefferi, A., Lasho, T. L., Powell, H. L., DeWald, G. W. & Kaufmann, S. H. (2006) Leukemia 20, 971-8.
28. Klusmann, J. H., Reinhardt, D., Hasle, H., Kaspers, G. J., Creutzig, U., Hahlen, K., van den Heuvel-Eibrink, M. M. & Zwaan, C. M. (2007) Leukemia 21, 1584-7.
29. Mizutani, E., Narimatsu, H., Murata, M., Tomita, A., Kiyoi, H. & Naoe, T. (2007) Bone Marrow Transplant 40, 85-7.
30. Fridman, J., Nussenzveig, R, Liu, P, Rodgers, J, Burn, T, Haley, P, Scherle, P, Newton, R, Hollis, G, Friedman, S, Verstovsek, S, and Vaddi, K. (2007) Blood (ASH Annual Meeting Abstracts) 110, 3538.
31. Verstovsek, S., Kantarjian, H, Pardanani, A, Thomas, D, Cortes, J, Mesa, R, Redman, J, Staschen, C M, Fridman, J, Vaddi, K and Tefferi, A. (2007) Blood (ASH Annual Meeting Abstracts) 110, 558.
32. Lannutti, B. J., Blake, N., Gandhi, M. J., Reems, J. A. & Drachman, J. G. (2005) Blood 105, 3875-8.
33. Chen, Z., Naveiras, O., Balduini, A., Mammoto, A., Conti, M. A., Adelstein, R. S., Ingber, D., Daley, G. Q. & Shivdasani, R. A. (2007) Blood 110, 171-9.
34. Hahn, C., Ross, K N, Kakoza, R M, Carr, S A, Du, J, Ong, S E, Golub, T R, and Stegmaier, K. (2007) Blood (ASH Annual Meeting Abstracts) 110, 209.
35. Mercher, T., Moore, S A, Cornejo, M G, Baudry-Bluteau, D, Cagnard, N et al. (2009) J. Clin. Invest. 199:852-864.

We claim:

1. A method for treating a patient having a proliferative blood or bone marrow disease or disorder, the method comprising administering to the patient an effective amount of a compound having a formula:

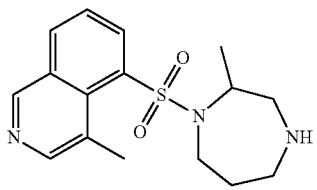 [SMILES: Cc1cncc2cccc(S(=O)(=O)N3CCCNCC3C)c12]

wherein the proliferative blood or bone marrow disorder is selected from a group consisting of an Acute Megakaryoblastic Leukemia, a Myeloproliferative Disease, a Myelodysplastic Syndrome, and an Acute Myeloid Leukemia.

2. The method of claim 1, wherein the effective amount is effective for inducing polyploidization of megakaryocyte cells in the patient, and the megakaryocyte cells are megakaryocyte progenitors.

3. The method of claim 1, wherein the effective amount is effective for inducing polyploidization of megakaryocyte cells in the patient, and the megakaryocyte cells are immortalized or dysplastic cells.

4. The method of claim 1, wherein the effective amount is effective for inducing polyploidization of megakaryocyte cells in the patient, and the megakaryocyte cells further are promoted to differentiate into platelet-producing cells.

5. The method of claim 1, wherein the patient has an Acute Megakaryoblastic Leukemia selected from a group consisting of AMKL associated with mutagenesis of GATA1 in Down syndrome, pediatric AMKL associated with a (1:22) translocation, and adult AMKL associated with mutations in JAK2 or JAK3.

6. The method of claim 1, wherein the patient has a Myeloproliferative Disease selected from a group consisting of primary myelofibrosis (PMF), essential thrombocythemia (ET), and polycythemia vera (PV).

7. The method of claim 1, wherein the effective amount is effective for increasing platelet counts in the patient.

8. The method of claim 1, wherein the compound haS a formula:

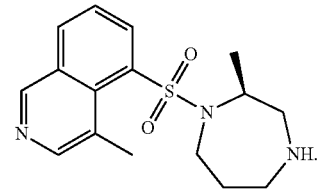 [SMILES: Cc1cncc2cccc(S(=O)(=O)N3CCCNC[C@@H]3C)c12]

9. The method of claim 1, wherein the compound has a formula:

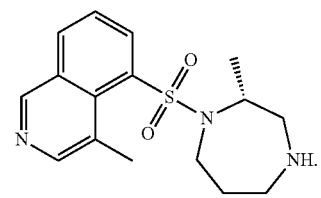

10. A method for treating a patient having Acute Myeloid Leukemia, the method comprising administering to the patient an effective amount of a compound having a formula:

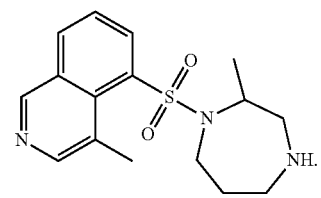 [SMILES: Cc1cncc2cccc(S(=O)(=O)N3CCCNCC3C)c12]

11. The method of claim 10, wherein the compound has a formula:
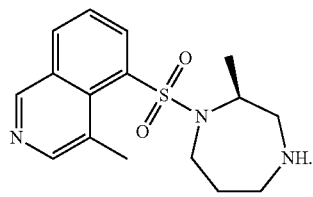 [SMILES: Cc1cncc2cccc(S(=O)(=O)N3CCCNC[C@@H]3C)c12]
12. The method of claim 10, wherein the compound has a formula:
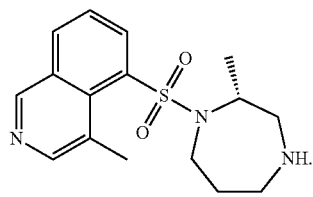 [SMILES: Cc1cncc2cccc(S(=O)(=O)N3CCCNC[C@H]3C)c12]
* * * * *